(12) United States Patent
Summit et al.

(10) Patent No.: US 9,032,982 B2
(45) Date of Patent: May 19, 2015

(54) CRUTCH APPARATUS AND METHOD FOR DESIGNING AND FABRICATING

(71) Applicant: 3D Systems, Inc., Rock Hill, SC (US)

(72) Inventors: Scott Summit, Mill Valley, CA (US); Kenneth B Trauner, San Francisco, CA (US)

(73) Assignee: 3D Systems, Inc., Rock Hill, SC (US)

( * ) Notice: Subject to any disclaimer, the term of this patent is extended or adjusted under 35 U.S.C. 154(b) by 12 days.

(21) Appl. No.: 13/849,522

(22) Filed: Mar. 24, 2013

(65) Prior Publication Data
US 2013/0247946 A1 Sep. 26, 2013

Related U.S. Application Data

(63) Continuation-in-part of application No. PCT/US2012/051612, filed on Aug. 20, 2012, which is a continuation-in-part of application No. 13/214,096, filed on Aug. 19, 2011, now abandoned, which is a continuation-in-part of application No. 12/820,968, filed on Jun. 22, 2010, which is a continuation-in-part of application No. 12/615,196, filed on Nov. 9, 2009, now Pat. No. 8,005,651.

(60) Provisional application No. 61/720,861, filed on Oct. 31, 2012, provisional application No. 61/785,903, filed on Mar. 14, 2013, provisional application No. 61/615,139, filed on Mar. 23, 2012, provisional application No. 61/112,751, filed on Nov. 9, 2008, provisional application No. 61/168,183, filed on Apr. 9, 2009, provisional application No. 61/185,781, filed on Jun. 10, 2009.

(51) Int. Cl.
| | |
|---|---|
| *A61H 3/02* | (2006.01) |
| *A61B 5/00* | (2006.01) |
| *H04M 1/725* | (2006.01) |
| *A61H 3/00* | (2006.01) |
| *A61H 3/04* | (2006.01) |
| *A63B 21/00* | (2006.01) |
| *A63B 59/00* | (2006.01) |

(Continued)

(52) U.S. Cl.
CPC ............ *A61H 3/02* (2013.01); *A61H 2003/006* (2013.01); *A61H 2201/0184* (2013.01); *A61H 2201/5094* (2013.01); *A61B 5/0064* (2013.01); *A61H 3/04* (2013.01); *A63B 21/1469* (2013.01); *A63B 21/1476* (2013.01); *A63B 59/0025* (2013.01); *G08B 21/0446* (2013.01); *A61H 2201/0161* (2013.01); *A61H 2201/10* (2013.01); *A61H 2201/1647* (2013.01); *A61H 2201/5071* (2013.01); *A61H 2201/5084* (2013.01); *A61H 2201/5097* (2013.01); *A61H 2230/60* (2013.01); *A61N 1/40* (2013.01); *H04M 1/72519* (2013.01); *H04M 1/72536* (2013.01); *H04M 2250/12* (2013.01)

(58) Field of Classification Search
CPC ....................................................... A61H 3/02
USPC ................. 135/65, 68, 71–73; 482/66–67, 75
See application file for complete search history.

(56) References Cited

U.S. PATENT DOCUMENTS

| | | | | |
|---|---|---|---|---|
| 3,213,869 A | * | 10/1965 | Frank | ............................... 135/71 |
| 5,178,595 A | * | 1/1993 | MacGregor | ..................... 482/75 |

(Continued)

FOREIGN PATENT DOCUMENTS

| | | | | |
|---|---|---|---|---|
| DE | 10308044 A1 | * | 9/2004 | ............... A61H 3/02 |
| FR | 2564738 A1 | * | 11/1985 | ............. A63C 11/22 |

(Continued)

*Primary Examiner* — Winnie Yip

(57) ABSTRACT

A crutch includes a grip and a forearm support that are coupled to an elongated member that extends from the forearm support to the ground. The inner surface of the forearm support can correspond to a digital representation of a forearm of the patient and the outer surface of the hand grip can correspond to a digital representation of a palmar surface of the patient's hand in at least a partially closed position.

20 Claims, 16 Drawing Sheets

(51) Int. Cl.
*G08B 21/04* (2006.01)
*A61N 1/40* (2006.01)

(56) References Cited

U.S. PATENT DOCUMENTS

| | | | | |
|---|---|---|---|---|
| 5,671,765 | A * | 9/1997 | Hagberg, Jr. | 135/68 |
| 6,494,919 | B1 * | 12/2002 | Matthews | 623/32 |
| 7,347,215 | B1 * | 3/2008 | Birnbaum | 135/66 |
| 7,503,337 | B1 * | 3/2009 | Morgan et al. | 135/70 |
| 2004/0055629 | A1 * | 3/2004 | Evans | 135/68 |
| 2009/0165834 | A1 * | 7/2009 | West | 135/65 |
| 2009/0235966 | A1 * | 9/2009 | Birnbaum | 135/66 |
| 2011/0099765 | A1 * | 5/2011 | Youssefieh | 16/430 |
| 2011/0126872 | A1 * | 6/2011 | Albertyn | 135/69 |

FOREIGN PATENT DOCUMENTS

| | | | |
|---|---|---|---|
| JP | 2008272389 | A * | 11/2008 |
| JP | 2010259618 | A * | 11/2010 |

* cited by examiner

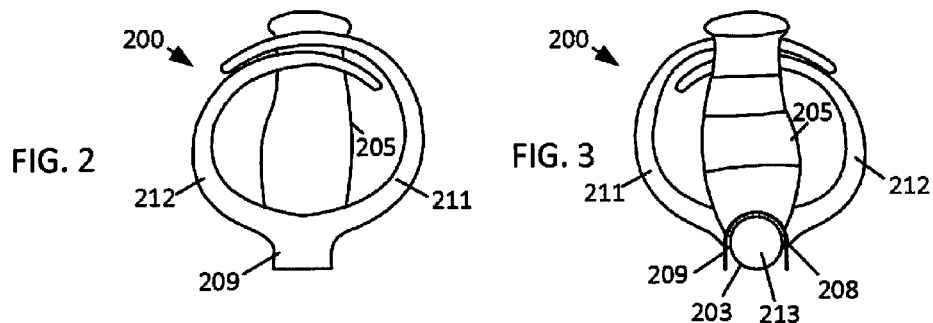
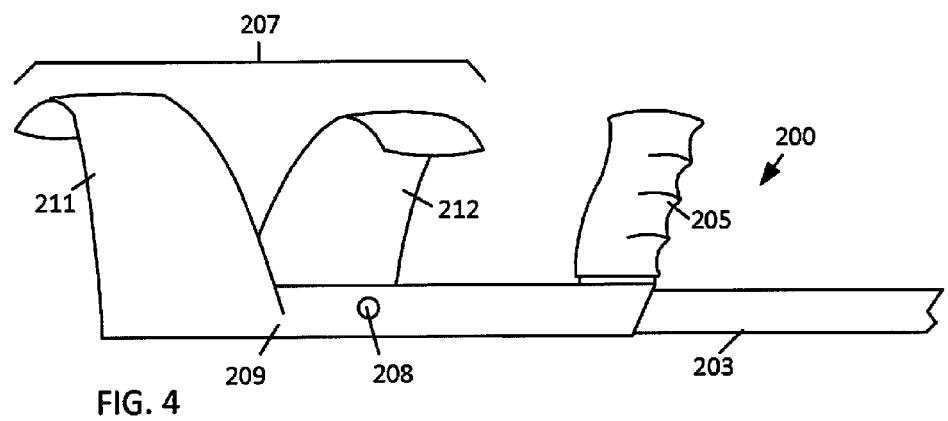
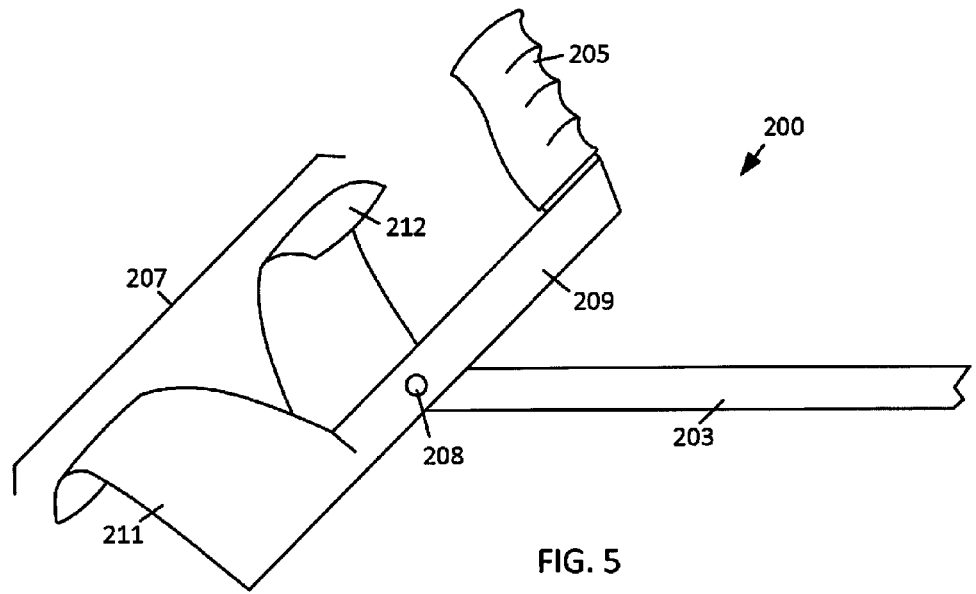

CRUTCH APPARATUS AND METHOD FOR DESIGNING AND FABRICATING

CROSS-REFERENCE TO RELATED APPLICATIONS

This application claims priority to U.S. Provisional Patent Application No. 61/785,903, "Spiral Brace And Method For Automated Spiral Brace Design" filed Mar. 14, 2013, U.S. Provisional Patent Application No. 61/615,139, "Unloading Structural Supports" filed Mar. 23, 2012 and U.S. Provisional Patent Application No. 61/720,861, "Spiral Brace" filed Oct. 31, 2012 and is a continuation-in-part of PCT Patent Application No. PCT/US2012/051612, "Adjustable Brace" filed Aug. 20, 2012 which claims priority to U.S. patent application Ser. No. 13/214,096, "Adjustable Brace" filed Aug. 19, 2011 which is a continuation-in-part of U.S. patent application Ser. No. 12/820,968, "Modular Custom Braces, Casts And Devices And Methods For Designing And Fabricating" filed Jun. 22, 2010 which is a continuation-in-part of U.S. patent application Ser. No. 12/615,196, now U.S. Pat. No. 8,005,651, "Custom Braces, Casts and Devices And Methods For Designing And Fabricating" filed Nov. 9, 2009 which claims priority to U.S. Provisional Patent Application No. 61/112,751, "Brace And Cast" filed on Nov. 9, 2008, U.S. Provisional Patent Application No. 61/168,183, "Orthopedic Braces" filed in Apr. 9, 2009, and U.S. Provisional Patent Application No. 61/185,781, "Bespoke Fracture Brace" filed in Jun. 10, 2009. The contents of PCT Application No. PCT/US2012/051612 and U.S. Patent Application Nos. 61/785,903, 61/615,139, 61/720,861, Ser. Nos. 13/214,096, 12/820,968, 12/615,196, 61/112,751, 61/168,183, and 61/185,781 are hereby incorporated by reference in their entirety.

BACKGROUND

In order to provide proper treatment of fractures, injuries and chronic conditions, there is a clinical need to protect the afflicted extremity from weight bearing forces. Current options for treatment of lower extremity pathologies include the use of crutches and instructing the patient not to apply weight bearing on the affected extremity. Frequently treatment is augmented with use of casting, bracing splinting. When range of motion of the extremity is required, a removable cast or splint is required that allows the injured joint to be moved actively or passively.

The Lofstrand crutch is a device that replaces a standard crutch and is different than a standard crutch because it includes a wrist or pistol grip mount and a semicircular forearm support. Lofstrand crutches are generally used by patients who are unable to bear the body weight load on the palms of their hands while using traditional crutches. These patients may need a Lofstrand crutch for various reasons including wrist arthritis, neurologic injury, decreased grip, wrist strength, etc. Crutches are typically manufactured and sold with a generic set of body contact structures and Lofstrand crutches of varied angles are commercially available with generic shapes. Because the forearm support is generic, forearm discomfort and instability of the forearm mounts is a frequent complaint of the devices. What is needed is an improved crutch with a forearm mount that inherently provides a better comfortable and stable fit around the patient's forearm.

SUMMARY OF THE INVENTION

A Lofstrand crutch includes a grip and a forearm support that are coupled to an elongated member that extends from the forearm support to the ground. The patient can place the forearm support around the forearm and grasp the grip. The grip and the forearm support can be coupled to a proximal portion of the elongated member and the distal end of the elongated member can be an elastic foot member that prevents the crutch from slipping when the foot is placed on the ground.

In different embodiments, the elongated member can be fixed in length or variable in length. For fixed length embodiments, the elongated member can be made of a single structure such as aluminum, fiberglass or carbon fiber and can be tubular in shape. In other embodiments, the elongated member can be variable in length and may have a telescopic configuration with an inner tubular structure mounted within an outer tubular structure. A locking mechanism can secure the inner tubular structure to a predetermined position within the outer tubular structure. This can be done with a pin and hole mechanism or any other suitable locking mechanisms. In other embodiments, the elongated member can include three or more concentric tubular structures which can allow the elongated member to retract into a much smaller structure when not being used.

In an embodiment, the grip and forearm support can be a single unitary structure made of a homogeneous material that is rigidly coupled to the elongated member. In other embodiments, the grip and forearm support can be separate structures that are independently coupled to the elongated member. In yet another embodiment, the forearm support can be coupled to the elongated member with a hinge that can have one or more locked positions. In the first locked position, the locking mechanism can rigidly hold the forearm support in the normal use position or angle relative to the elongated member. In an unlocked position, the hinge can allow the elongated member to rotate relative to the forearm support. In a second locked position, the locking mechanism can rigidly hold the forearm support in the second use position or angle relative to the elongated member that is different than the normal use position.

The hand grip can be designed from digital images of a pliable material that has been grasped by the patient's hand. The patient can then release the pliable material which can retain the impressions made by the hand. The pliable material can then be photographed to obtain a digital representation of the hand impression in the pliable material can be obtained as described below. The digital representation of the hand impression can then be used to design the outer surface of the hand grip.

The forearm support can also have inner surfaces that correspond to digital representations of the patient's body. In order to design a Lofstrand crutch having a custom forearm support, the forearm may first be photographed. One or more colored stickers can be applied to the patient's limb and a plurality of markings or points of visible or IR light can be projected to the patient's limb. The light sources can project a pattern of light spots onto the limb. The limb can be placed on a positioning stand between a plurality of infrared (IR) and/or visible light cameras. A doctor may mark the injured areas of the limb with a pen, stickers or any other suitable markers or markings that provide a suitable contrast to the skin of the patient. Some of the markers or markings can be used for position detection or anatomical features such as joints, knuckles, specific areas of bones, etc. Markers or markings can also indicate the areas where the patient is injured such as bone breakage, or swollen areas, etc. Other markers or markings can indicate a desired edge or a seam of the forearm support. These markers or markings can be captured by the digital photographic images and the marking locations can be used to design the forearm support and hand grip.

From the photographs, a three dimensional digital representation of the arm and/or hand can be created by photogrammetry, image correlation, depth mapping or any other suitable IR and/or visible light photography based surface topography detection method.

From the three dimensional representation of the limb surface topography, a forearm support can be designed having an inner surface that corresponds to the three dimensional digital representation of the patient's limb. The inner surface of the forearm support and design can be asymmetrically offset from the digital representation of the patient's arm and hand. For example, a first curved member of the forearm support can have a thumb section that has a first offset and the second curved member can have a second offset. The first offset may be less than the second offset. The offsets can be positive or negative in relation to the principle digital representation of the arm. In the case of a positive offset, the offset is raised above the principle digital representation of the arm in the region of the offset. In the case of a negative offset, the offset is lowered below the principle digital representation of the arm in the region of the offset. In an embodiment, the positive and negative offsets can range from about 1-3 mm.

In an embodiment, the forearm support has a smooth inner surface that conforms to the digital representation of the scanned surface of the limb and closely matches the surface measurements of the patient's body. Because the inner surface of the forearm support accurately conforms to the patient to provide a very close fit, the surface of the arm matches the inner surface of the forearm support. Thus, the forearm support can be used by the patient without any padding. The forearm support can be made of a hard plastic material that provides structural strength to support the forearm but can also be flexible to allow the forearm support to be elastically deformed to allow a user to place the forearm support on the forearm. In order to be comfortable, the inner surface of the hard plastic forearm support should also be very smooth. In an embodiment, the inner surface can have a surface finish of less than 500 $R_a$ µinch. In an embodiment, the innermost surface of the structural layer of the forearm support can be made of a homogeneous plastic material. In other embodiments, the entire forearm support can be made of a homogeneous plastic material. A forearm support that can be worn by a patient without inner surface padding has several benefits including: simplified forearm support design and construction, less material for fabrication, lower weight, lower profile thickness, better ventilation, no absorption of water, easier cleaning, etc.

The inventive custom design process is unique because it provides a virtual fitting of the hand grip and the forearm support to the patient prior to fabrication of the actual device. Because the innermost surfaces of the forearm support can be designed to be a very close fit to the patient, no additional padding may be needed. No other known system provides the ability to design custom hand grip and forearm supports in a virtual manner. In particular, the inventive process can detect markers and/or markings placed on a body and utilize this information to design the forearm supports based upon the location of the marks. Although the forearm support and the hand grip are described with reference to Lofstrand crutch, in other embodiments these components can be used with other devices such as a Lofstrand walker, exercise equipment, sporting goods, hand tools, firearms, device controls, etc.

BRIEF DESCRIPTION OF THE DRAWINGS

FIG. 2 illustrates a proximal end view of an embodiment of a Lofstrand crutch;

FIG. 3 illustrates a distal end view of an embodiment of a Lofstrand crutch;

FIGS. 4-5 illustrate side views of an embodiment of the proximal portion of the Lofstrand crutch;

DETAILED DESCRIPTION

The present invention is directed towards Lofstrand devices in which a hand grip and forearm mounts that each include surfaces that contact the patient's body. The patient contact areas of the hand grip and forearm mounts are designed and fabricated to conform to the patient's forearm and wrist anatomy and morphology. Lofstrand crutches are designed to load the forearm rather than traditional crutches that load the palm. Because the present invention is directed towards a patient specific crutch design, the forearm support of the crutch can be design to conform to the forearm of the patient and avoid boney prominences on the patient.

Figure 1:
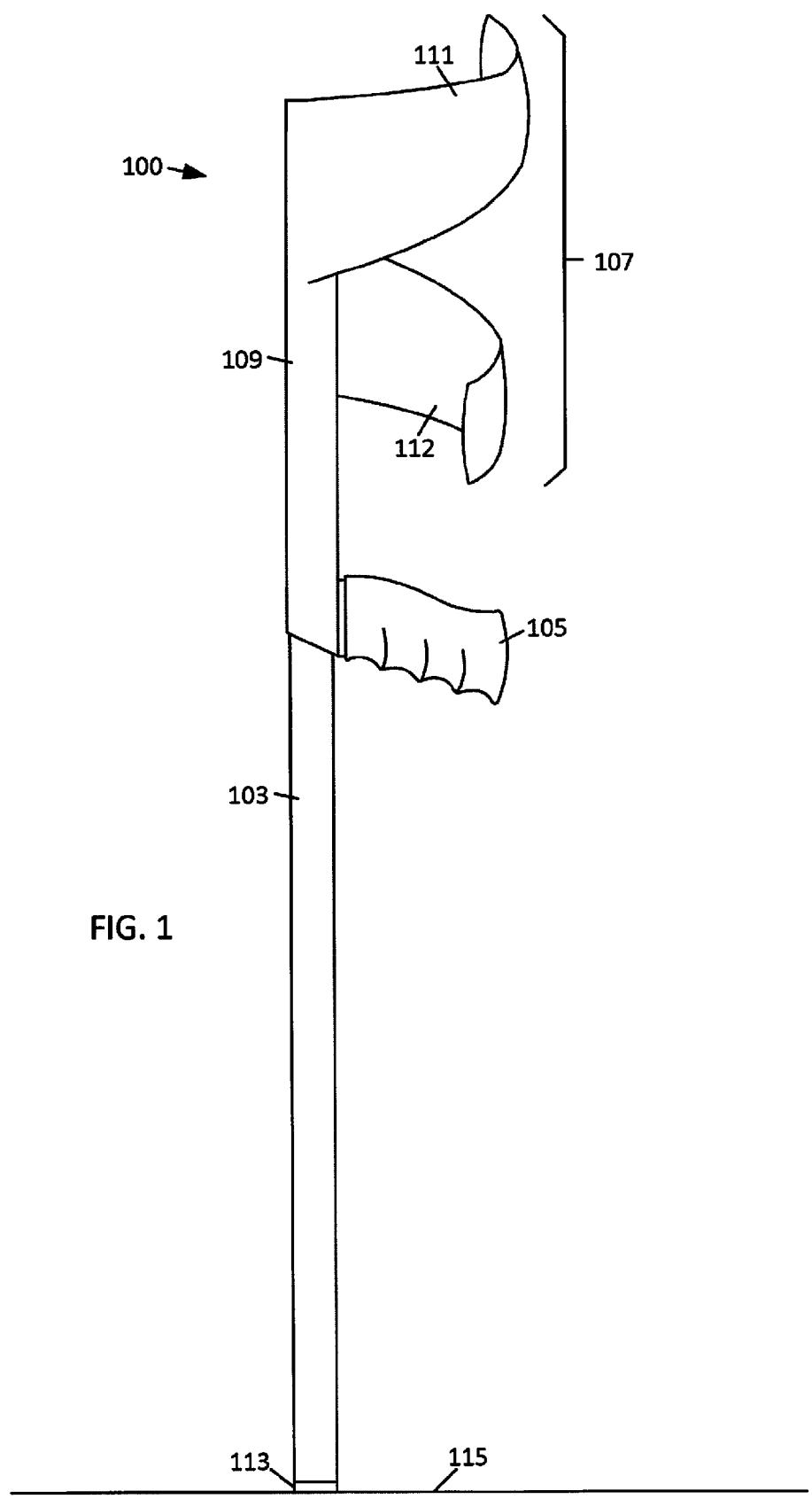
FIG. 1 illustrates a side view of an embodiment of a Lofstrand crutch.

With reference to FIG. 1, an embodiment of a Lofstrand crutch 100 is illustrated. The illustrated Lofstrand crutch 100 includes an elongated member 103, a hand grip 105 and a forearm support 107. A non-slip foot 113 can be coupled to the distal end of the elongated member 103 which can prevent the crutch 101 from sliding when the foot 113 is placed against the ground 115 the proximal portion of the elongated member 103 can be coupled to the hand grip 105 and forearm support 107. The elongated member 103 can include a first curved member 111 and a second curved member 112 that at least partially surround the forearm of the patient. The hand grip 105, first curved member 111 and the second curved member 112 can be rigidly attached to an elongated body 109. In the illustrated embodiment, the first curved member 111 can be attached to a proximal portion of the elongated body 109, the second curved member 112 can be attached to a more central portion of the elongated body 109 and the hand grip 105 can be attached to a distal portion of the elongated body 109. The elongated member 103 can be coupled to a distal portion of the elongated body 109. In an embodiment, the first curved member 111 and the second curved member 112 define a spiral configuration. The elongated member 103 can surround the proximal end of the elongated member 103 wherein the spiral configuration wraps more than one full turn around the limb of the patient wherein an inner surface of the forearm support corresponds to a digital representation of the forearm of the patient When a patient uses the illustrated Loftstrand crutch 100, the forearm is placed within the first curved member 111 and the second curved member 112 and the hand grasps the hand grip 105. The first curved member 111 and the second curved member 112 can define a spiral configuration, wherein the spiral configuration wraps more than one full turn around the forearm of the patient wherein an inner surface of the forearm support corresponds to a digital representation of the forearm of the patient.

The patient can walk with one crutch 100 on each arm. The patient can pressing the foot 113 of the elongated member 103 of one of the crutches 100 against the ground 115 forward of the patient. This can at least partially support the patient's body weight with the arm that holds the crutch 100. The patient can then move one of the legs forward. The patient can then move the second crutch 100 forward and then take the next step with the other leg. This process can be repeated to allow the patient to walk.

In FIG. 1, the elongated member 103 is fixed in length and the angle of connection with the hand grip 105 and the forearm support 107. In other embodiments, the elongated member can be adjustable in length and the elongated member may also have an adjustable angle relative to the forearm support and hand grip. With reference to FIGS. 4-7, another embodiment of the inventive Lofstand crutch is illustrated. In this embodiment, the elongated member 203 is attached to an elongated body 209 with a hinge 208 that allows the elongated member 203 to rotated relative to the elongated body 209. The hand grip 205 and the forearm support 207 are rigidly coupled to the elongated body 209. The forearm support 209 can include the first curved member 211 and the second curved member 212. The elongated body 209 can have a partially open construction that partially surrounds the elongated member 203. The elongated body 209 can be coupled to the elongated member 203 with a hinge 208 that allows the elongated body 209 to rotate relative to the elongated member 203.

FIG. 2 illustrates a view of the Lofstrand crutch 200 from the proximal end and FIG. 3 illustrates a view from the distal end. The first curved member 211 and the second elongated member 212 are coupled to the elongated body 209 and can wrap at least one full turn around the forearm of a patient. The inner surface of the first curved member 211 and the second curved member 212 can correspond to a digital representation of a patient's forearm. This matching fit between the forearm support 207 and the patient can provide a more comfortable fit and reduce the possibility of injury to the patient. As illustrated in FIGS. 2 and 3, the first curved member 211 and the second curved member 212 can have a variable thickness. In the illustrated embodiment, the thickness of the first curved member 211 and the second curved member 212 is greater at the junction with the elongated body 209 that at the opposite ends. This can allow the first curved member 211 and the second curved member 212 to have non-uniform flexibility such that they are more rigid at the portions closer to the elongated body 209 and more flexible at the opposite ends.

FIG. 4 illustrates a side view of the crutch 200 with the elongated member 203 aligned with the elongated body 209. The first curved member 211 and the second curved member 212 can define a spiral configuration, wherein the spiral configuration wraps more than one full turn around a forearm of the patient. FIG. 5 illustrates a side view of the crutch 200 with the elongated member 203 at an angle relative to the elongated body 209. The rotated positions can be helpful to a patient by providing additional operational load bearing flexibility. When the elongated body 209 of the forearm support 207 are aligned with the elongated member 203, the weight applied by the crutch can be primarily applied to the palm of the hand against the hand grip 205. However, when there is an angle between the forearm support 207 and the elongated member 203, the weight transmitted by the crutch can be distributed between the forearm support 207 and the hand grip 205. When the elongated body 209 of the forearm support 207 is perpendicular to the elongated member 203, substantially all of the force from the elongated member 203 can be applied to the forearm of the user. By adjusting the angle of the forearm support 207 relative to the elongated member 203, the balance of forces applied to the user's hand and forearm can be controlled.

For example, the patient may need to use the crutch 200 to move from a seated position to a standing position. The patient can use the crutch 200 in the angled position to help move out of the seated position. Once standing, the patient can change the crutch 200 to a normal position with the elongated member 203 aligned with the elongated body.

Figure 6:
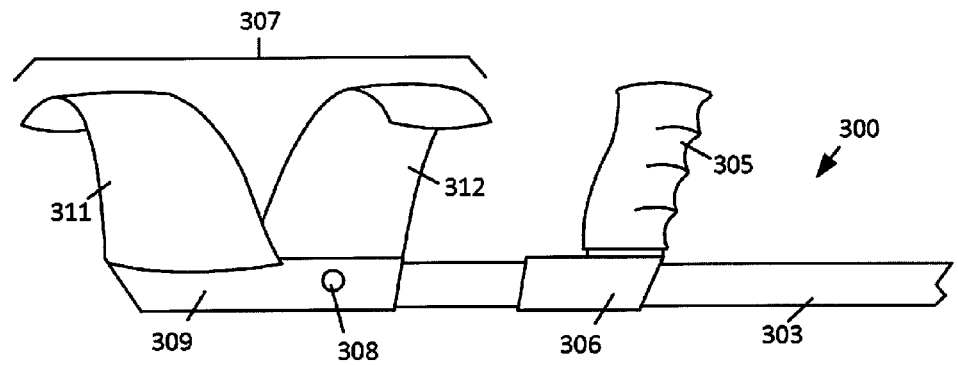
FIGS. 6-7 illustrate side views of an alternative embodiment of the proximal portion of the Lofstrand crutch.
Figure 7:
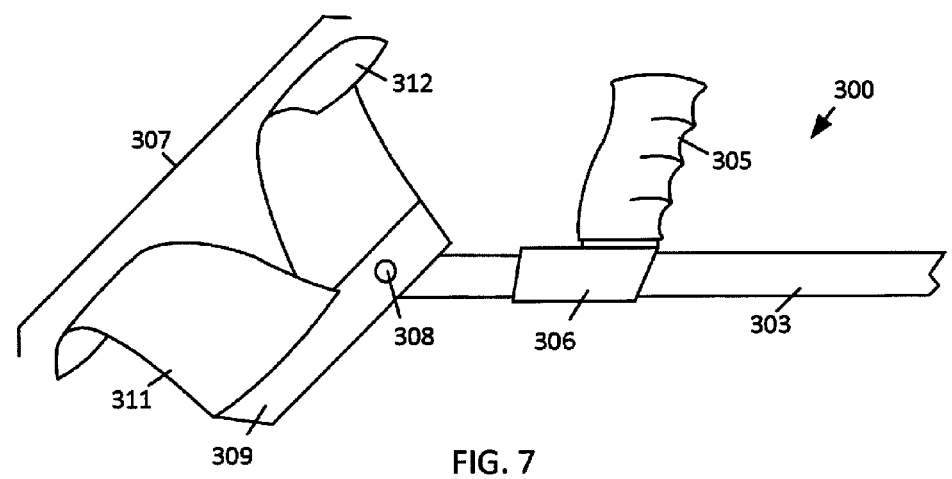

FIGS. 6 and 7 illustrate side views of another embodiment of the Lofstrand crutch 300. In this embodiment, the hand grip 305 can be rigidly coupled to the elongated member 303 rather than the elongated body 309. When the elongated member 303 rotates relative to the elongated body 309, the hand grip 305 moves with the elongated member 303 rather than the elongated body. 309. The first curved member 311 and the second curved member 312 can be rigidly attached to the elongated body 309 and may rotated with the elongated body 309.

Figure 8:
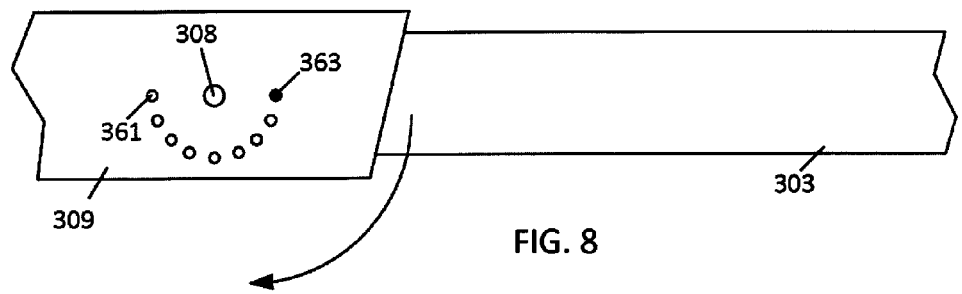
FIGS. 8-10 illustrate side views of an embodiment of a rotation locking mechanism for the elongated member.
Figure 9:
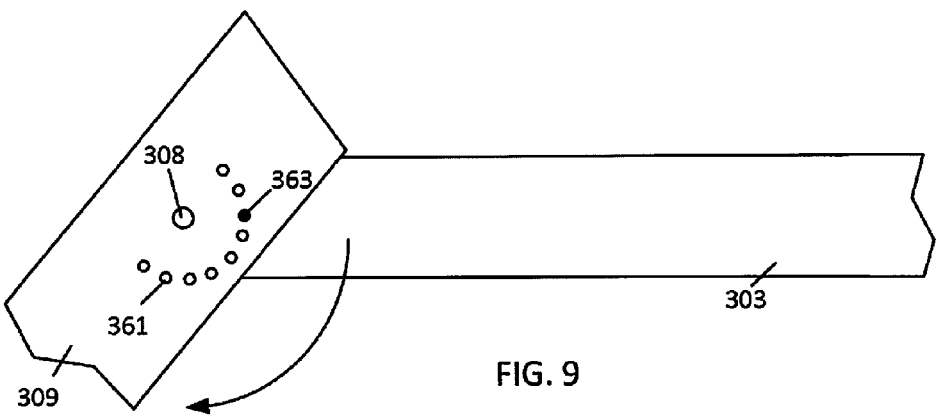
Figure 10:
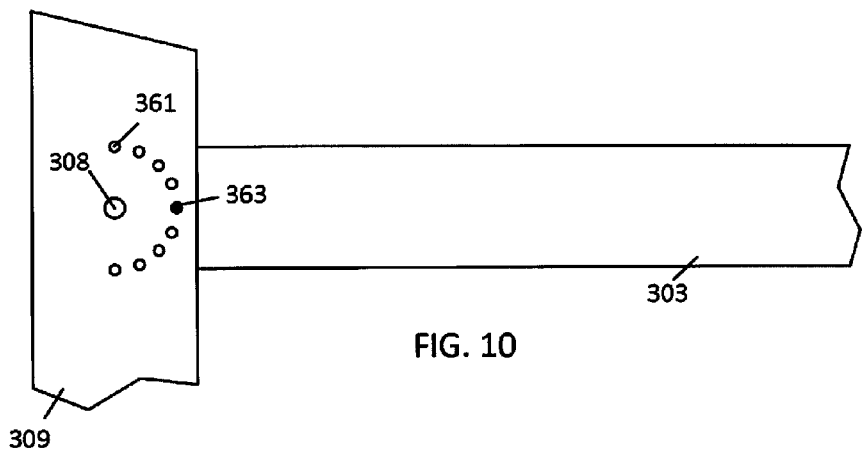

With reference to FIGS. 8-10, in some embodiments, the Lofstrand crutch can include a locking mechanism that can rigidly hold the elongated member 203 at predetermined set angles relative to the elongated body 309 and the forearm support. The elongated member 203 can be coupled to the elongated body 309 with a hinge 208. The elongated body 309 may include a plurality of locking holes 361 that can each be the same radial distance from the hinge 208. In the illustrated embodiment, the locking holes 361 are arranged in a semicircular pattern in the elongated body 309. The elongated member 303 can include a spring loaded pin 363 that extends through one of the locking holes 361. In order to change the angle of the elongated member 303 about the hinge the user can depress the pin 363 and rotate the elongated member 303 until the pin 363 is at the desired and the pin 363 is aligned with the corresponding locking hole 361. The user can then release the pin 363 so the pin extends through the corresponding locking hole 361.

With reference to FIG. 8, the elongated member 303 can be aligned with the elongated body 309 but the user wishes to change the angle. The user can press the spring loaded pin 363 out of the locking hole 361 and rotate the elongated body 309 as shown in FIG. 9. Once the elongated body 308 is in the desired angle the user can release the spring loaded pin 363 which can extend through the corresponding locking hole 361 which can cause the elongated member 303 to be locked at a different angle relative to the elongated body 309 as shown in FIG. 10. In different embodiments, the inventive crutch can have different ranges of angular adjustability. For example, in an embodiment, the elongated member 303 can rotate within an angular range between about 0-15 degrees. In other embodiments, the elongated member 303 can rotated within an angular range of about 0-120 degrees. The range of adjustment angles can be based upon the needs and/or preferences of the patient.

Figure 11:
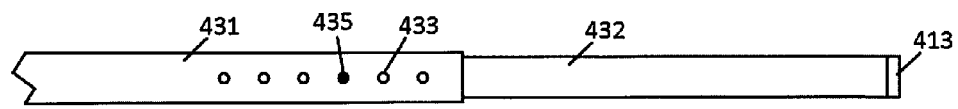
FIGS. 11-13 illustrates views of an embodiment of an adjustable length elongated member.
Figure 12:
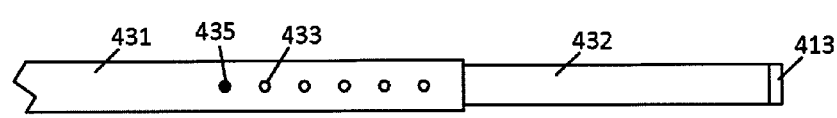
Figure 13:
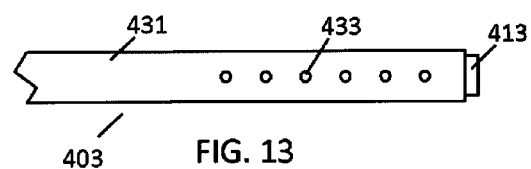

In some embodiments, it can be desirable to have a Lofstrand crutches that have elongated members that are variable in length. FIGS. 11-13 illustrate an embodiment of the elongated member 403 that has a telescopic configuration and includes a first tube 431 that surrounds the outer diameter of a second tube 432. A foot 413 can be coupled to the distal end of the second tube 432 and the proximal portion of the second tube 432 can include a spring loaded locking pin 435 that extends through one of the locking holes 433 in the distal portion of the first tube 431 as shown in FIG. 11.

The user can adjust the length of the elongated member 403 by pressing the spring loaded locking pin 432 inward and moving the second tube 432 within the first tube 431. The user can then release the locking pin 432 when the elongated member 403 is at the desired telescopic length. In some embodiments, it may be desirable to collapse the elongated member 403 as much as possible. In this embodiment, the user can press the locking pin 432 inward and slide the second tube 342 completely into the first tube 431. If the user wishes to re-extend the elongated member 403, the user can pull the second tube 432 out of the first tube 431 and extend the locking pin 435 into the locking hole 433 that correspond with the desired length.

Figure 14:
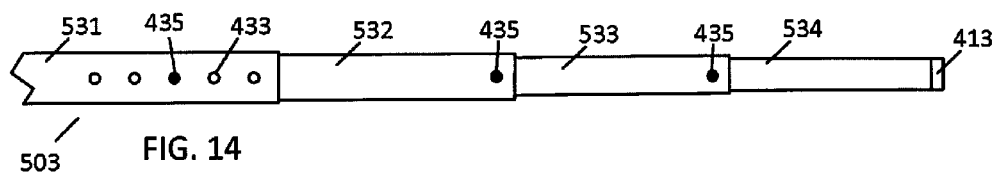
FIGS. 14-16 illustrates views of another embodiment of an adjustable length elongated member.
Figure 15:
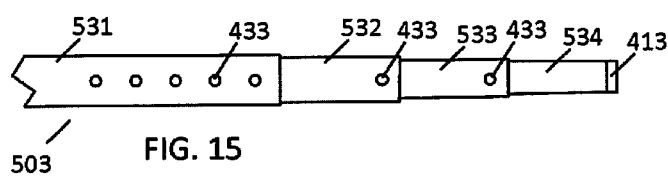
Figure 16:
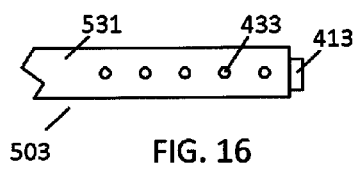

In other embodiments, it is possible to have an elongated member that includes more than two telescopic tubes. With reference to FIGS. 14-16, an embodiment of the telescopic elongated member 503 is illustrated that includes four concentric tubes 531, 532, 533, 534. In the illustrated embodiment, the first telescopic tube 531 includes a plurality of locking holes 433 and the second, third and fourth telescopic tubes 532, 533, 534 can each include one or more locking holes 433. In the normal position, the locking pins 435 extend through one of the locking holes 433 in each of the telescopic tubes 531, 532, 533, 534. The user can alter the length of the elongated member 503 by altering the position of the locking pin 435 in the plurality of locking holes 433 in the first telescopic tube 531 without changing the positions of the locking pins 435 in all other tubes 532, 533, 534 as shown in FIG. 14. If the user wishes to collapse the elongated member 503, the locking pins 435 can all be retracted and the second, third and fourth tubes 532, 533, 534 can be compressed into the first tube 531. This compacted configuration can significantly reduce the overall length and size of the crutch which can be useful for storage when the crutch is not being used or needs to be shipped or transported.

Another feature of the inventive Lofstrand crutch is the hand grip. In an embodiment, the hand grip can be a generic ergonomic design. However, in order to improve patient comfort, the hand grip can alternatively have an outer surface that corresponds to a digital representation of the palmar surface of the patient's hand. In an embodiment, a plurality of photographs of the palmar surface of the hand in a closed position can be obtained and these photos can be used to create a three dimensional digital representation of the hand which can be used to design the outer surface of the hand grip. However, in other embodiments, a substantially different process can be used to obtain the digital representation of the palmar surface of the patient's hand.

Figure 17:
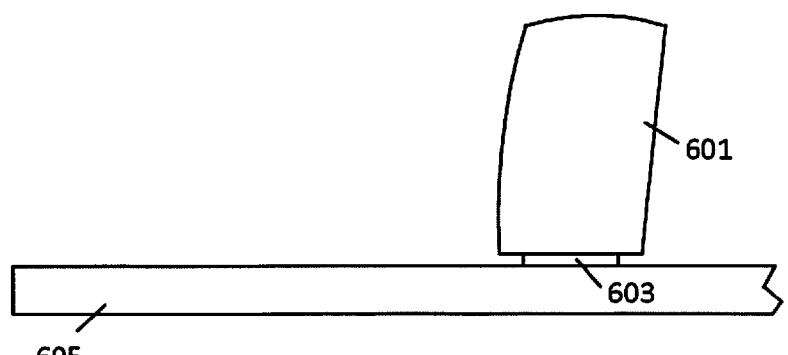
FIGS. 17-21 illustrate a sequence of process steps for designing a hand grip.

With reference to FIG. 17 an elongated piece of pliable material 601 can be provided. The pliable material 601 can be any material that will plastically deform such as modeling clay, putty, pliable plastic, wax, etc. In some embodiments the pliable material 601 can be in a tubular form placed around a rigid cylindrical structure 603 that is mounted on a base 605.

Figure 18:
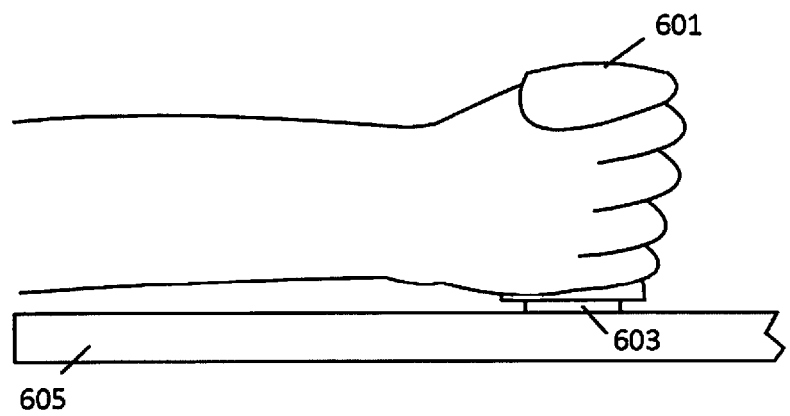

With reference to FIG. 18, the patient can grasp and squeeze the pliable material 601 until it deforms into a shape of the palmar surface of the hand. The hand pressure on the pliable material 601 should not be too tight since this will be the design of the hand grip. The hand pressure may be less than 20 PSI. If the pliable material 601 placed over a rigid cylindrical structure 603, the hand pressure should not cause any portion of the rigid cylindrical structure 603 to be exposed or have a thickness less than a predetermined minimum value of about 5 mm.

Figure 19:
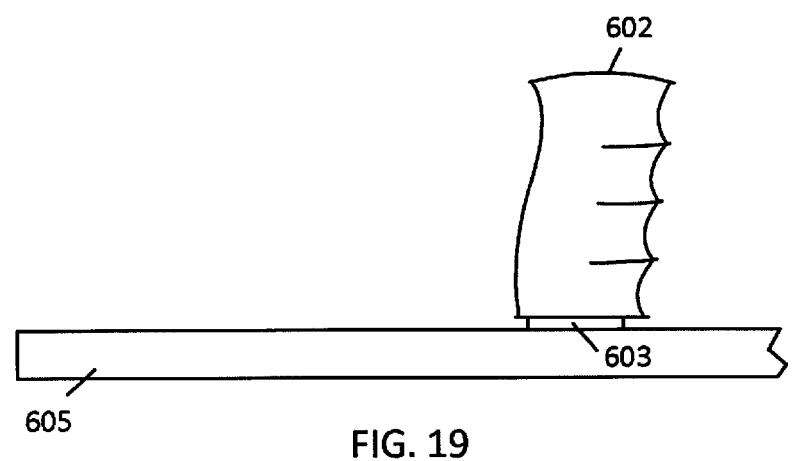
Figure 20:
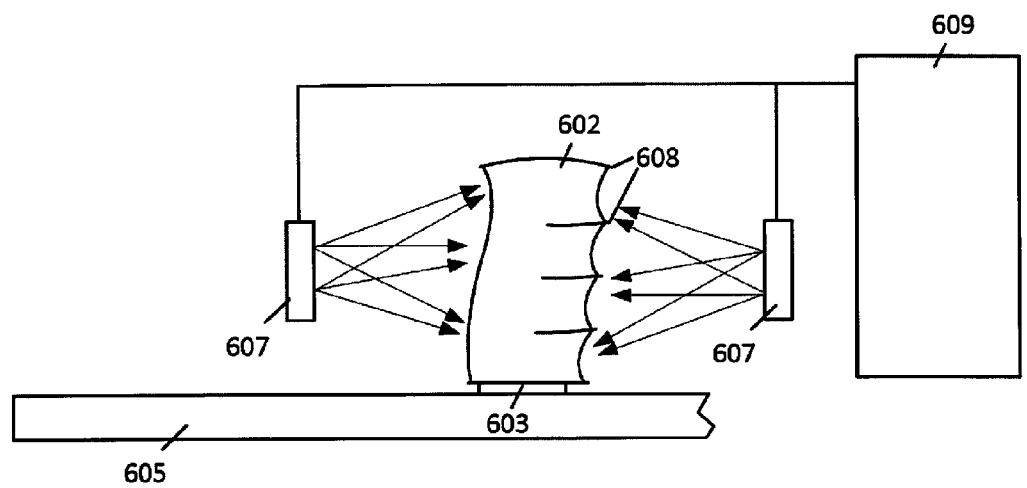
Figure 21:
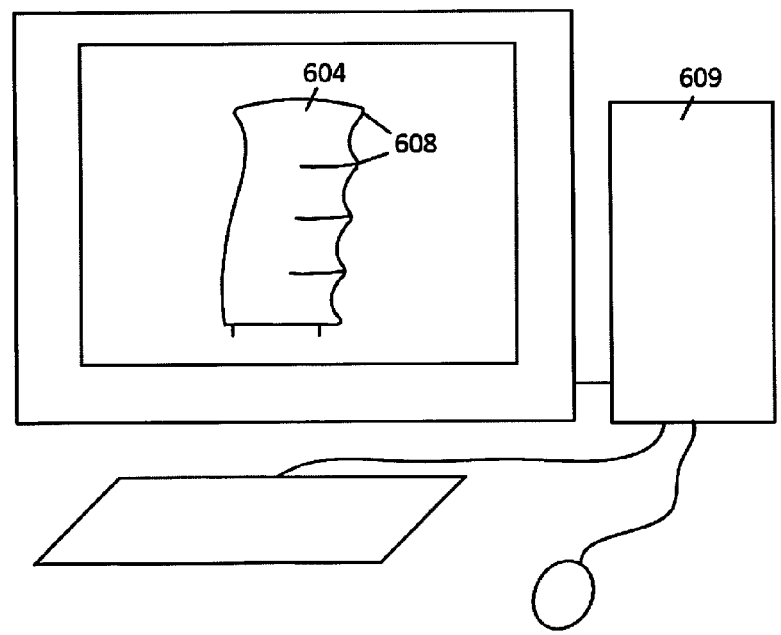

With reference to FIG. 19, the patient has released the grip and the deformed pliable material 602 has a surface that corresponds to the palmar surface of the patient's hand. With reference to FIG. 20, photographs of the deformed pliable material 602 can be taken with a plurality of digital cameras 607. The digital images of the deformed pliable material 602 can be stored in a memory of a computer 609. With reference to FIG. 21, the digital images can be processed and a virtual digital hand grip design 604 can be created based upon the digital images of the deformed pliable material 602. The hand grip design 604 can be slightly different than the exact surface of the deformed pliable material 602 (FIG. 20). For example, if the deformed pliable material 602 has any sharp edges or features 606 (FIG. 20), the hand grip design 604 can replace these sharp surfaces with rounded surfaces 608 which will not cause injury or discomfort to the patient. In an embodiment, the design system can automatically convert any surfaces that have a radius of less than 0.1 mm to a radius of at least 0.5 mm. The hand grip can be fabricated with an outer surface that matches the hand grip design 604.

In addition to having a custom hand grip, the inventive can also include a forearm support that has an inner surface that can correspond to a digital representation of the forearm so that the forearm support will provide a custom and personal fit for the patient's limb. The forearm support can be fenestrated to allow the limb to be exposed to ambient air. This ventilation can allow perspiration from the limb to evaporate rather than being trapped between the limb and the forearm support. In an embodiment, the curved members of the forearm support can have thickness that is between about 0.05 inch and 0.50 inch. In an embodiment, the pitch or the spacing along the axis between the curved member of the forearm support can be greater than about 2 inches and less than about 6 inches. The proximal portion of the forearm support can have a width of the body between about 0.5 inch and 2 inches. Because the forearm support is thin and light weight and may look more like an ornamental object than a medical device, the patient will be more likely to use the inventive crutch. For clearer figures, the fenestrations have not been illustrated in the forearm support illustrations. However, in embodiments, the fenestrations can be a pattern or small or larger holes of any cross-sectional shape that extend through the thickness of the forearm support and allow air to circulate to the portions of the limb covered by the forearm support. Examples of fenestrations are shown in U.S. patent application Ser. No. 12/823, 512 which is incorporated by reference in its entirety. The fenestrations in the forearm support may also allow the curved members of the forearm support to deflection in selective planes to adapt to the conformation of the forearm.

Although the forearm support has been described as not having padding on the interior surfaces, in some embodiments, elastic padding may be formed on the interior surfaces. Although the forearm support has been described as not having padding attached to the inner surfaces, in other embodiments, the inner surfaces of the forearm support can have padding on some of the inner surfaces. For example, the forearm support can have padding selectively applied to the inner surfaces along the ulnar border, ulnar styloid, distal dorsal radius to improve comfort. In an embodiment, the padding can be produced with a three dimensional printer by printing a plurality of elastic features on the inner surfaces of the forearm support where padding is needed or desired. In an embodiment, the padding on the inner surface can be deposited an elastic material by the three dimensional printer which can print a different material for the structural components of the forearm support. In another embodiment, the padding on the inner surfaces can be deposited using the same material as the structural portions. However, while the structural material can be constructed from solid material, the padding can be in the form of a plurality of features that have flexible surfaces that provide a padded inner surface.

Figure 22:
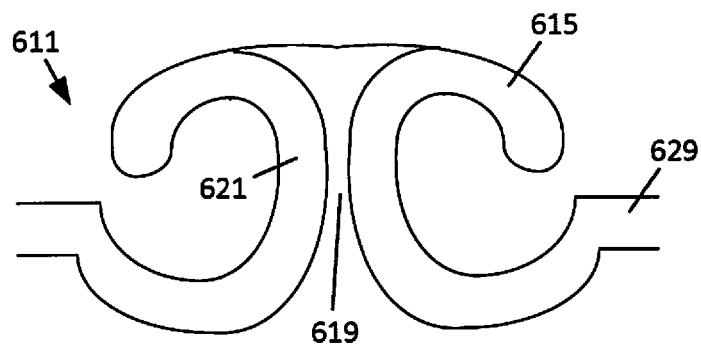
FIGS. 22-24 illustrate cross section views of an embodiment of a compressible pad element for the inner surface of the forearm support.
Figure 23:
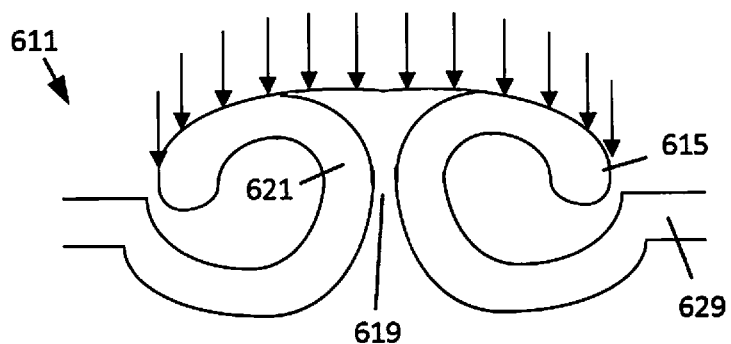
Figure 24:
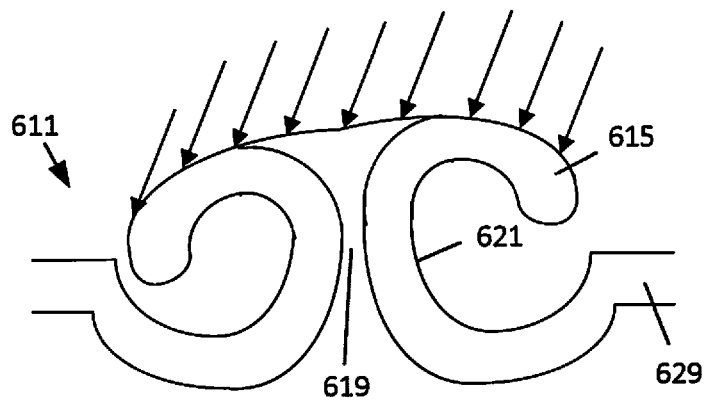

With reference to FIGS. 22-24, another feature that can be designed into the forearm support is a dense grid of individually suspended contact pads 611 involves each pad 611 being 'hollow', giving it the shape of a torroid. This allows contact 'rings' 615 to contact the skin, each contract pad 611 can have a ventilation hole 619 at the center. The ventilation holes 619 gives improved airflow to the skin. The 'doughnut' shape of it makes window edema less likely, since there are no hard edges to press against the skin to disturb the blood flow. And the relatively large contact pad 611 area will likely increase the comfort against the skin. Air will also flow around each of the contact pads 611, and can be evacuated through a perforation pattern through the outer wall. This will increase comfort to the user and cool the surface skin temperature.

Because each of the contact pads 611 may be created as an individual revolved 'cell', it can be created so that a 'well' exists around each of the pad's 'stocks'. Beyond the 'well', the wall thickness grows, since the thick parts of the cells intersect adjacent cells. This allows a relatively strong structure to be created that is flexible where desired (around the stocks of each pad), yet strong where desired (in between each stock). Both strength and compliance is met in a single surface. This contact point on a stalk approach distributes the skin contact over many individual points. These point contacts minimize the area of decreased circulation by allowing blood flow to the skin between the contact points. The compresses area can thus receive blood supply by diffusive processes. This strategy minimizes the potential for larger ischemic zones or areas of skin breakdown. In addition, by varying the mechanical properties of the stalk that supports the contact point the amount of shear stress at the skin can be minimized. If the stalk is sufficiently flexible, with motion of the skin within the forearm support, motion will not occur between the contact point and the forearm support but instead will occur at the level of the stalk, between the contact pads and the exoskeleton outer layer of the forearm support. By minimizing shear and ischemia, such a padded structure can minimize the potential for skin breakdown.

For dynamic forearm supports, these contact pad 611 constructs can be produced as a coherent volume of attached structures, or for more dynamic forearm supports, the contact pads 611 may be printed as discrete elements in continuity with the outer exoskeleton and ventilation pattern, but whereby the contact pads 611 and support structure exclusive of the exoskeleton are not in contact. Such a construct would allow for differing motions in select regions of the forearm support without any impact on the mechanical properties due to the contact pads.

The pads 611 illustrated in FIGS. 22-24 are part of the inner surface of the forearm support. Each pad 611 is flexible and movable in compression as well as horizontal movement. In an embodiment, the pads 611 each have a contact portion 615 and a stem 621 that is coupled to a frame. When the pad 611 is compressed against a portion of the patient's body, for example when the forearm support is worn by the patient, the contact portion 615 is compressed against the stem 621 which is compressed against the frame 629. The stem 621 can be much narrower than the contact portion and bendable. When the contact portion 615 of the pad 611 moves horizontally, the stem 621 will bend in response to the pad 611 movement. The stem 621 is also coupled to the frame 629 in such a way that the stem 621 can move in a perpendicular direction relative to the plane of the frame 629. Thus, the pad 611 can move in response to any perpendicular compression of the pad 611 against the frame of the forearm support. In an embodiment, a portion or the entire interior surfaces of the forearm support can include the described pads 611. The pads 611 used in a forearm support can all be identical or each can have a different design characteristics. For example, the pads 611 located over harder surfaces such as bones under the skin can have flexible pads 611 that allow for comfortable movement of the bones and/or joins. In contract, the pads 611 that are located over softer areas of the body can have stiffer since the soft areas may not require as much padding. FIG. 22 illustrates a cross section of an example of a single pad 611 element. FIG. 23 illustrates the pad 611 in direct compression and FIG. 24 illustrates the pad 611 in diagonal compression. In the compressed illustrations, the stem 621 bends in response to the pressure applied to the pad 611.

In other embodiments, different flexible pad designs can be used including non-circular surfaces, different spring stems and different ventilation mechanisms. The hardness or softness of the pads can be quantified by the spring rate of the stem against the frame and the contact area of the pad. A pad with a large contact area and a low spring rate will be very soft. In contrast, a pad with a small contact area and a high spring rate will be a harder pad. The equation quantifying the hardness or softness of the pads is (pad surface area)×(stem spring rate)=X. For example, if the pad area is 1 square inch and the spring rate is 10 lb per inch, when the pad is compressed ¼ inch into the frame, the force will be 2.5 lbs per square inch. If the pad is compressed ½ inch into the frame the force will be 5 lbs per square inch. The dynamic hardness/softness characteristics of each of the pads can be individually designed into the forearm support. The pad areas can range from about ¼ square inch to about 5 square inches and the spring rate of the stem can range from about 0.01 lb/in to about 100 lb/in or more.

Figure 25:
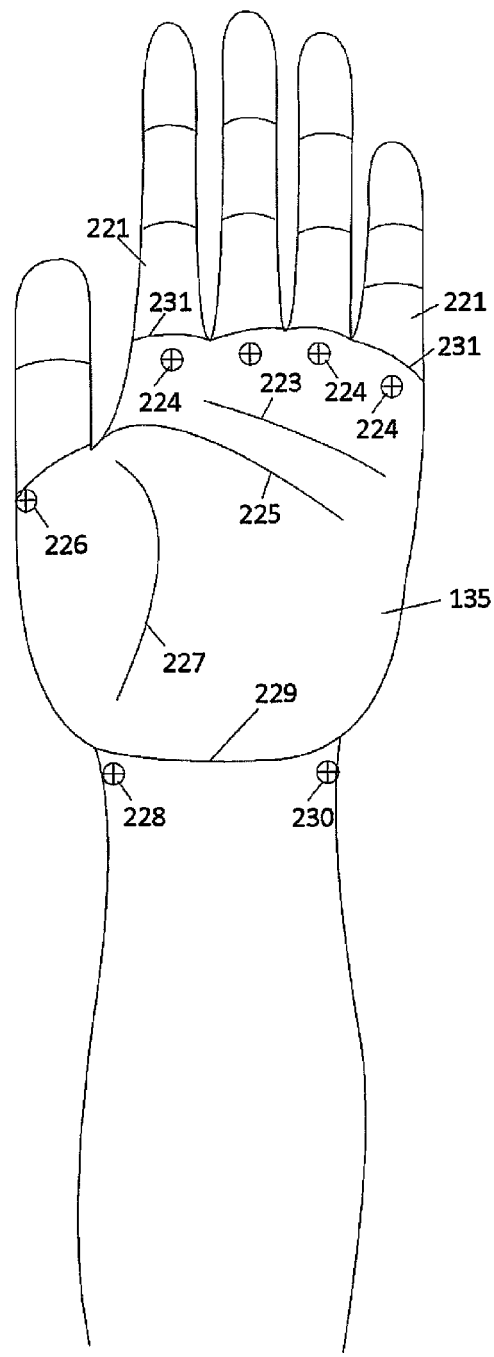
FIGS. 25-26 illustrate dorsal and palmar views of a hand and forearm.
Figure 26:
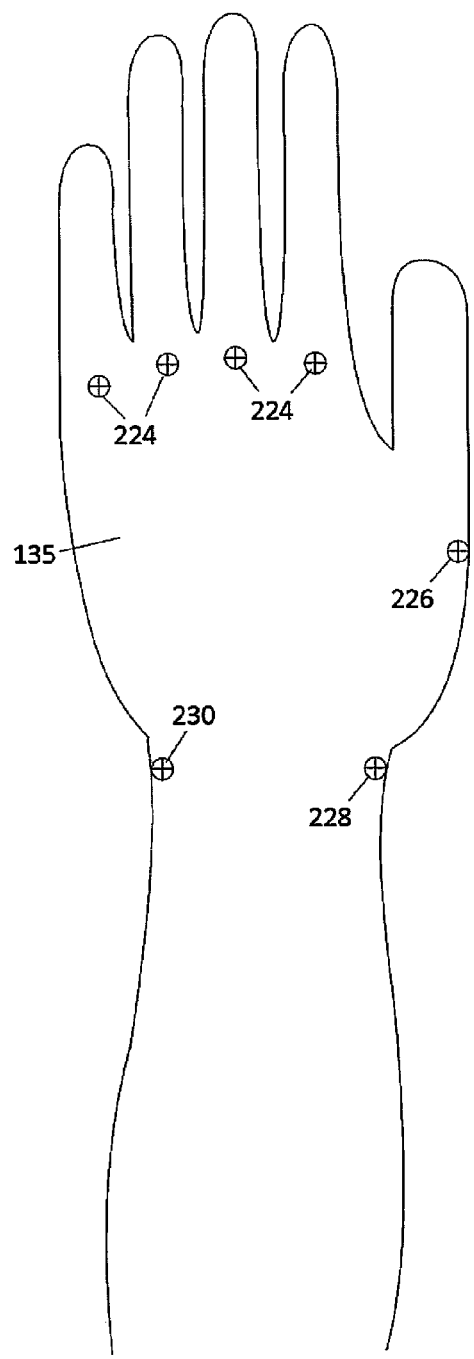

With reference to FIGS. 25 and 26, a hand and specific anatomical structures are illustrated. FIG. 25 illustrates a palmar side of the hand and FIG. 26 illustrates a dorsal side of the hand 135. The anatomical structures include: the proximal phalanx segments 221 of the fingers, the palmar digital creases 231, the distal palmar crease 223, the proximal palmar crease 225, the thenar crease 227 and the wrist crease 229. Because the fingers bend towards the palmar side of the hand 135, these creases may only be visible on the palmar side of the hand 135. The hand 135 may also include anatomical points that can be marked with stickers or any other type of markings that can improve the accuracy of the measurements for these points. These marked anatomical points can include: finger knuckles 224, the thumb knuckle 226, radial styloid 228, and the ulnar styloid 230. The knuckle and styloid points may be marked on either side of the hand. In an embodiment, the knuckle and styloid points can be marked on one side of the hand 135 and the system can identify these points and points for these anatomical features on the opposite side of the hand. For example, if the knuckle and styloid points are identified on the surface of the dorsal side, the system can process this information and also identify the locations of the knuckle and styloid points on the surface of the opposite palmar side of the hand 135. The system can also function in the reverse manner with the system identifying points marked on the dorsal side of the hand based upon markings on the palmar side of the hand In an embodiment, the system can use the location information to design a portion or the entire the forearm support. The system can design the forearm support either with additional input from a designer or fully automatically.

By identifying and referencing these visible anatomical features of the hand during the design process, the forearm support can be designed to cover specific areas of the arm and avoid certain areas of the arm. In an embodiment, the photographic process used to create a digital representation of the body may be able to identify these features and provide graphical identifications of these features on a display coupled to a design computer. In an embodiment, this information can also be used to automatically design the entire forearm support.

In different embodiments, additional sensors and/or transducers can be incorporated into the described devices. The sensors can provide information about the patient and the use of the crutch. For example, a pressure sensor in the hand grip can provide feedback regarding the use of the crutch by the patient and the pressure of the hand grip on the patient's hand. If the use of the crutch is required for physical therapy, the recording of the use of the crutch can be used to verify the required physical activity. If the pressure exceeds a predetermined safe value, the system can transmit a signal to a warning device that can instruct the patient to correct the user of the device. In an embodiment, the crutch may include an accelerometer that can normally detect the gravitational acceleration in a vertical direction. If a patient and crutch fall, the accelerometer can detect the gravitational force has a side force rather than a vertical force. This change in accelerometer output can cause the crutch to emit an alarm signal, which can inform a help service provider that the patient may need, assistance. The hand grip may contain control assemblies or control electronics. These electronics may contain wireless communication technology, batteries and microprocessors to control exoskeletal devices or other remote electronic related devices.

An industrial designer using a Computer Aided Design (CAD) computer program can design the forearm support and hand grip. The mechanical data for a patient can be obtained from visible or infrared (IR) light photographs of the patient's limb. This body topography can be determined from the photographs and the topography data is then digitized and input into a CAD program that is referenced to design the forearm support and hand grip. An example of a suitable CAD program is Pro/Engineer by Parametric Technology Corporation. Other CAD software includes: SolidWorks by SolidWorks Corporation a subsidiary of Dassault Systèmes, S. A. The forearm support can be a hard and strong structure that is designed to surround the limb.

For example, the forearm support and hand grip can be created for a patient using a CAD system. The forearm support can have an interior surface that matches the mechanical dimensions and surface contours of the patient's arm. In order to accurately create an interior surface that matches the patient's arm, the surface counters of the user's arm are measured. The measurement of the outer surface of the arm can be obtained in several different ways. In a preferred embodiment, a photogrammetric, depth mapping or image correlation technique or other type of photographic surface detection method is used to obtain the outer surface measurements which can be a set of 3-dimensional coordinates that define the outer surface of the patient's arm or any other body part.

Photogrammetry in its broadest sense reverses the photographic process by converting flat 2-dimensional images of objects back into the real 3-dimensional object surface. Two or more different photographs can be required to reconstruct a 3-dimensional object. In a perfect photogrammetry process, two photographs would provide enough information to perfectly reconstruct the 3-dimensional object. Unfortunately, the photography and measuring process are generally not perfect so the reconstruction of the 3-dimensional object based upon two photos will also have defects. The photogrammetry object measurement process can be improved by taking more photographs and using the extra information to improve the accuracy. The photogrammetry process will produce a set of 3-dimensional coordinates representing a surface of an object from the measurements obtained from the multiple photographs.

Photogrammetry uses the principle of triangulation, whereby intersecting lines in space are used to compute the location of a point in all three, XYZ dimensions. In an embodiment, multiple cameras are used to photograph the leg or body part simultaneously. In other embodiments, a light from a light source that is a known distance from a camera is projected onto a patient and a photograph of the patient is taken. By triangulating each of the points of light, the distances from the camera to each point of light can be determined. In order to triangulate a set of points one must also know the camera positions and aiming angles also called the "orientation" for all the pictures in the set. A process called resection is used to determine the camera positions and aiming angle calculations for each camera. The cameras should also be calibrated so their errors can be defined and removed.

Triangulation is the principle used by photogrammetry to produce 3-dimensional point measurements. By mathematically intersecting converging lines in space, the precise locations of the points can be determined. Photogrammetry can simultaneously measure multiple points with virtually no limit on the number of simultaneously triangulated points. By taking pictures from at least two or more different locations and measuring the same target in each picture a "line of sight" is developed from each camera location to the target. Since the camera locations and aiming directions are known, the lines can be mathematically intersected to produce the XYZ coordinates of each targeted point. When a pattern of IR or visible light points are projected onto the patient, triangulation can also be used to determine the locations of these points based upon the distance between the light source and the camera and the detected angles of the points.

Resection is the procedure used to determine the coordinates of the object from photograph data, based upon the camera positions and aiming directions, also known as the orientation of the camera. Typically, all the points that are seen and known in XYZ coordinates in the image are used to determine this orientation. For an accurate resection, you may have at twelve or more well-distributed points in each photograph. If the XYZ coordinates of the points on the object are known, the camera's orientation can be computed. It is important to realize that both the position and aiming direction of the camera are needed for resection. It is not sufficient to know only the camera's position since the camera could be located in the same place but be aimed in any direction. Consequently, the camera's position which is defined by three coordinates, and where it is aimed which is defined by three angular coordinates must be known. Thus, although three values are needed to define the X, Y and Z coordinates of a target point, six values may be required to define a point on a picture, XYZ coordinates for position, and XYZ angles for the aiming direction.

The surface being photographed should also have a minimum number of well-distributed reference points that appear on each photograph and for an accurate surface measurement. The reference points can be visible marks placed on the object that provide a visible contrast that will be clearly shown on the photographs. There should be at least twelve well-distributed reference points on each photograph and at least twenty points for the entire surface of the object. The reference points should be evenly distributed on the object and throughout the photograph. The surface of the object can be more accurately measured with a larger number of reference points.

In an embodiment, the patient's natural features including: freckles, spots, wrinkles, pores and other features can be used as the reference points. Alternatively, IR or visible light can be projected onto the patient to provide a pattern or a random distribution of many projected light points on the patient, which are then photographed to provide reference points for surface topography measurements. Any of these types of points can be used alone or in combination. For example, a surface detection method may include projecting a plurality of IR light points onto a patient and place one or more stickers on the patient. Photographs of the patient can detect both the locations and/or positions of the light points and the stickers. The stickers may provide more contrast with the patient and measurements taken from the stickers may result in more accurate location measurements. Thus, the stickers may be used to one or more important locations on the limb. It is also possible to mark the patient's skin with ink markers, stickers, and the like and in an embodiment, the patient or patient's limb can be covered with a form fitting material such as an elastic cotton tube, stockinet, leotard, or body suit.

In an embodiment, a computer program processes the photographic measurements to produce the final XYZ coordinates of all the measured points. In order to do this, the program triangulates the target points and resects the pictures. The program may also calibrate the camera. Typical accuracies of the three dimensional measurements can be very high under ideal operating conditions. For example, the measurements can be accurate to 50-100 microns (0.002" to 0.004"). However, the accuracy of a photogrammetric measurement can vary significantly since accuracy depends on several inter-related factors. Important accuracy factors include: the resolution and quality of the camera, the size of the object being measured, the number of photographs taken, and the geometric layout of the pictures relative to the object and to each other.

Photogrammetric measurements can be dimensionless. To scale a photogrammetric measurement, at least one known distance is required. The known distance can be a distance marked on the object, a known distance between cameras or a known distance between a light source and a camera. For example, if the actual coordinates for some targeted points are known, the distances between these points can be determined and the points can be used to scale the measurement. Another possibility is to use a fixture with targets on it and measure the fixture along with the object. Because the distance between the targets on the fixture is known, it can be used to scale the other measurements between reference points on the object. Such fixtures are commonly called scale bars. The patient topography dimensions can also be determined by knowing a distance between two cameras and the angles of lines between the cameras and the points on the patient. From this information, the distances between the cameras and the points on the patient can be determined by triangulation. Similarly, the patient topography dimensions can also be determined by knowing a distance between a light beam source and a camera, an angle of the light beams from a source and the angles of the light points detected by the camera. From this information, the distances between the camera and the light points on the patient can be determined by triangulation. The light can be infrared and the camera can be an infrared camera that produces infrared photographs. The surface measurement information obtained from the photographs can be used to generate a digital representation of at least a portion of the patient.

In an embodiment, the inventive method is used to make a support for a limb. A series of photos are taken of the limb. If the bone is broken, fracture should be reduced before the photos are taken. The photogrammetric processing methods described above are then used to obtain the surface coordinates of the limb. In order to define common surface points on the limb, reference points can be placed on the limb. The reference points can simply be any contrasting color points, patterns, shapes, objects, symbols or other optical indicators that are easily visible. The reference points can be black or colored ink marks that are placed on the body with a pen. In other embodiments, the reference points can be lights such as visible light, infrared light, points or grids, stickers or objects or any other visible point of reference. For example, circular adhesive stickers that have a contrasting color can be placed on the patient and photographed. The stickers can provide accurate reference points, which can be used to produce the digital representation of the patient's limb and/or body. In the preferred embodiment, the reference points are placed and evenly distributed around the entire limb that the forearm support is being constructed for.

Figure 27:
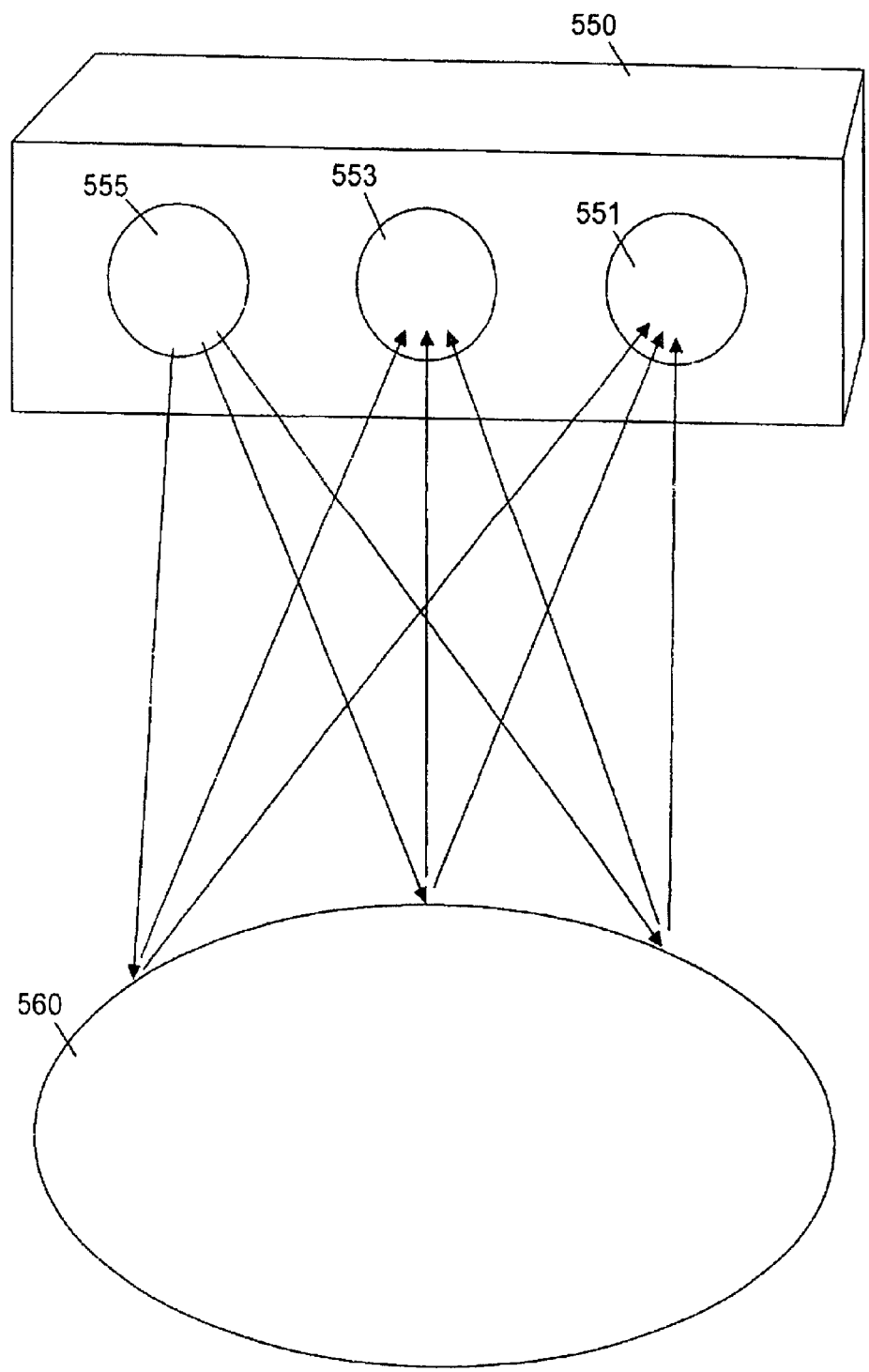
FIGS. 27-29 illustrate IR and visible light photographic systems for detecting a surface of a patient.

With reference to FIG. 27, in an embodiment the three dimensional surface data of a patient can be obtained using an optical device comprising a color image camera 551, an infrared (IR) camera 553 and an infrared (IR) light source 555 coupled to a signal processor. The IR light source 555, IR camera 553 and color image camera 551 can all be mounted on one side of the optical device 550 so that the color camera 551 and IR camera 553 have substantially the same field of view and the IR light source 551 projects light within this same field of view. The IR light source 555, IR camera 553 and color image camera 551 can be mounted at fixed and known distances from each other on the optical device 550. The color image camera 551 can provide color information for the patient's limb 560 or portion of the patient within the viewing region of the camera 551. The IR camera 553 and IR light source 555 can provide distance information for each area of the patient's limb 560 exposed to the IR light source 555 that is within the viewing region of the IR camera 553. The infrared light source 555 can include an infrared laser diode and a diffuser. The laser diode can direct an infrared light beam at the diffuser causing a pseudo random speckle or structured light pattern to be projected onto the patient's limb 560. The diffuser can be a diffraction grating that can be a computer-generated hologram (CGH) with a specific periodic structure. The IR camera 553 sensor can be a CMOS detector with a band-pass filter centered at the IR laser wavelength. In an embodiment, the color image camera 551 can also detect the IR light projected onto the patient's limb 560.

Figure 28:
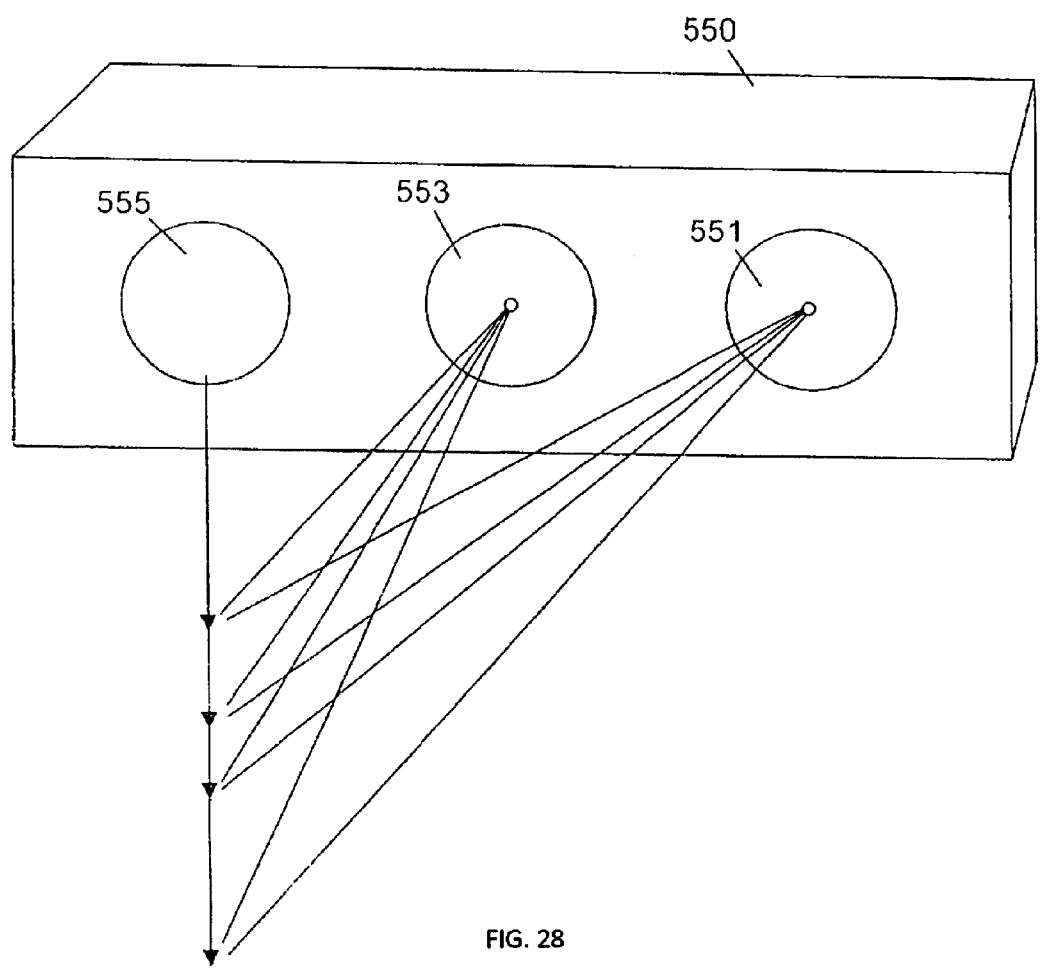

With reference to FIG. 28, the optical device 550 can detect the distance between the infrared camera 553 and the IR light on the patient because the camera 553 sees the patient's limb at a different angle than the infrared light source 555 and the distance between infrared light source 555 and IR camera 553 is defined. The principle of structured light distance sensing is that given a specific angle between IR light source 555 and IR sensor 553 for each point of light on the patient's limb and a distance between the object and the IR light source 555 or IR camera 553 or color camera 551 can be determined by triangulation. The angles of the light points on the patient's limb detected by the IR camera 553 and the color camera 551 will change depending upon the distance of the patient from the optical device 550. In an embodiment, a calibration process can be used to determine the angles of each light point on a plane at different distances from the optical device 550. By knowing the angles and corresponding distances for each point of IR light and distance of the points of light from the optical device 550 can be determined. These distance calculations for an object can also be known as three dimensional mapping. The distance value for each light point can also be matched with the visible color image data so that color and distance information for each pixel of a patient image can be determined and stored.

Because a single picture can capture the patient in a fixed position, the IR light source 555 can project the IR light on the patient and the IR camera 553 can take a single photograph of the patient 560. The color camera 551 may also simultaneously take a single photograph of the patient's limb 560. In other embodiments, multiple IR or color photographic images can be taken of the patient's limb 560 in different positions and the corresponding image shifts are directly related to distance from the camera. Each successive photographic image is served as a reference photograph for the next frame calculation so that the movement of the patient can be detected and the changes in the three dimensional mapping can be recorded.

Figure 29:
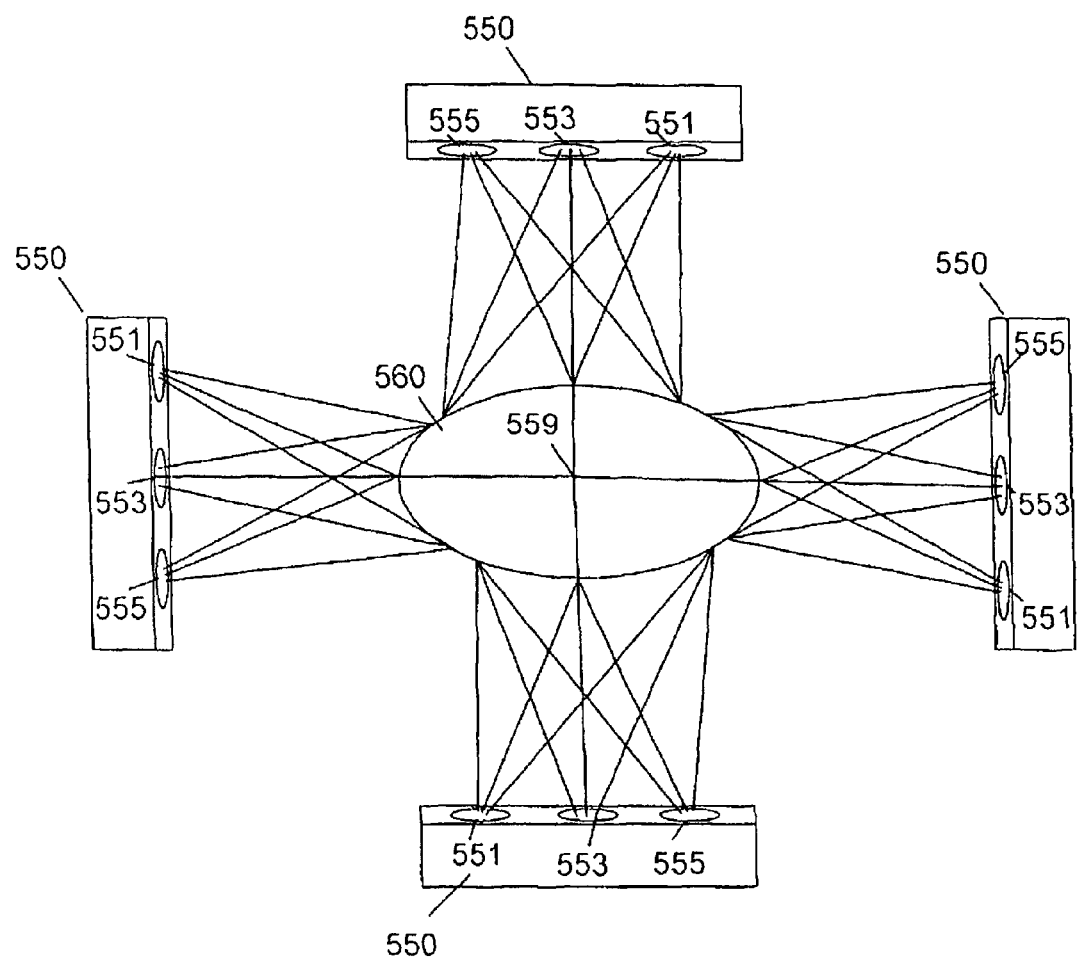

As discussed, the IR camera can detect the light pattern projected onto the patient's limb and through triangulation, the distance between the IR camera and color camera and each point of the light pattern on the patient can be determined. However, the distance information for the points can only determine a three dimensional surface of the patient's limb or a portion of the patient's limb that are detected by the IR camera 553 or the color camera 551. With reference to FIG. 29, in order to determine a three dimensional surface around a patient's limb, multiple optical devices 550 can be placed around the patient and the three dimensional surface information from each of these cameras can be combined to determine the three dimensional surfaces around a circumference of a patient's limb which can be a digital representation of the limb of the patient. In an embodiment the IR light from each of the IR light sources 555 can be emitted simultaneously and the photographs from all of the IR cameras 553 and color cameras 551 can be taken simultaneously. In other embodiments, the IR light sources 555 can interfere with the IR cameras 553 that are not part of the same optical system 550. Rather than projecting IR light from all of the IR light sources 555 at the same time, the optical systems 550 can be configured to sequentially illuminate with IR light and photograph the patient's limb 560. A first optical system 550 will emit the IR light and take IR and color photos of the patient's limb 560. The first optical system 550 can then stop projecting IR light onto the patient's limb 560 and the second optical system 550 can then emit the IR light, take IR and color photos of the patient's limb 560. The second optical system 550 can then stop projecting IR light onto the patient's limb 560. This described process can be sequentially repeated for the remaining optical systems 550.

After taking the IR photographs, surface data for different sides of the patient's limb 560 can be combined from the optical systems 550 in various different ways. For example, the multiple IR cameras 553 can produce distance information for the photographed patient's limb 560 that can be combined using a photogrammetry process to determine a full or partial circumferential three dimensional representation of the patient's limb 560. The surface data from the optical systems 550 will include some of the same surface areas of the patient's limb 560 that were also captured by at least two of the adjacent optical system 550. Because the three dimensional shape data is the same, the system can identify these matching surface shapes and combine the surface data to obtain continuous surface data for the photographed portion of the patient's limb 560. In an embodiment, the optical systems 550 can be aligned around the patient 560 with the IR cameras 553 radially aligned in a planar manner and directed towards a center point 559 within a cross section of the patient's limb 560. The optical systems 550 can each produce surface data for a portion of the patient's limb 560. Because the IR photos are taken on a common plane, the surface data from the different optical systems 550 can be joined by determining the distance of the surface data from the center point 559. In an embodiment, a first set of calibration IR and/or color photographs can be taken by the optical systems 550 of a physical center point marker 559 without the patient's limb 560. IR and/or color photos can then be taken of the patient 560. From this information, the position of the center point 559 relative to the surface data or digital representation of the patient 560 can be determined. By knowing the distances and alignment of the surface data to a common center point 559, the surface data from the different optical systems 550 can be combined. In an embodiment, the optical systems 550 can be arranged on direct opposite sides of the patient's limb 560. Although four optical systems 550 are shown, in other embodiments, two or more optical systems 550 can be used to obtain the surface data for the patient's limb 560. Three optical systems 550 may be required to have some overlapping surface data for the patient's limb 560.

Figure 30:
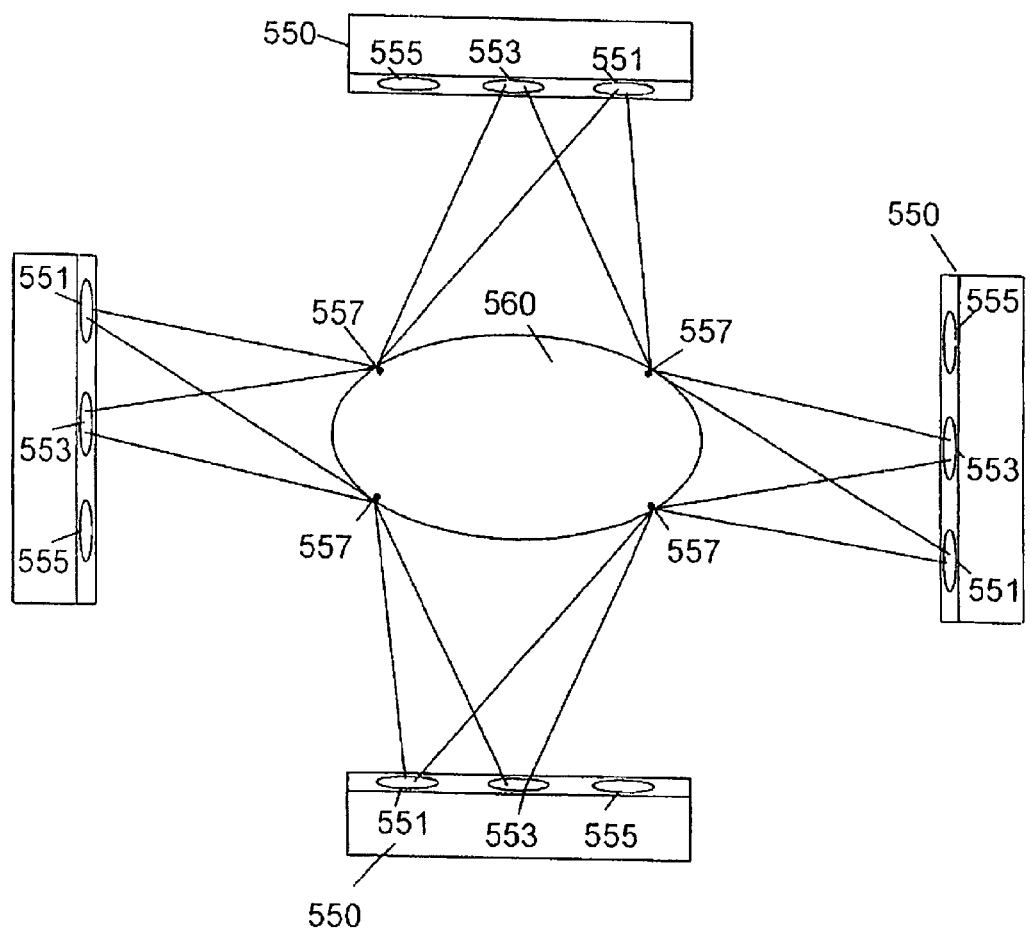
FIG. 30 illustrates a marked patient for detection by the photographic detection system.

With reference to FIG. 30, in other embodiments the surface data from the optical systems 550 can be combined by using alignment markings 557 on the patient's limb 560. The patient's limb 560 may be covered with a material and a visible or IR marking 557 can be projected onto the patient's limb 560 at locations that are within the field of view of two or more optical systems 550. The color camera 551 may detect both visible and IR markings and the IR camera 553 may only detect IR markings. The optical systems can be able to distinguish the IR light from the IR markings because the shape of the IR marking 557 can be larger or may have a different shape. The surface data from adjacent optical systems 550 can be combined by using a photogrammetry or image correlation process that matches the positions of the markings 557 that are photographed by both optical systems 550.

Figure 31:
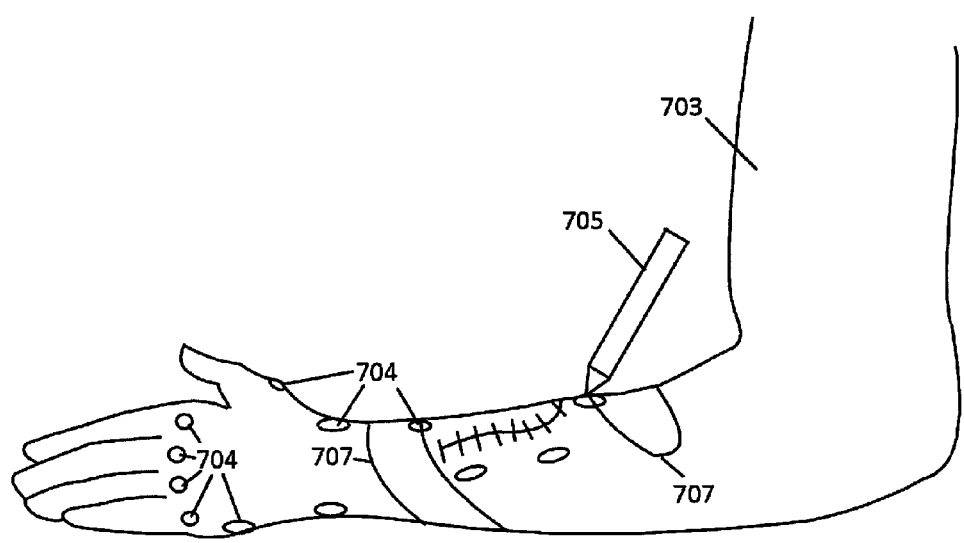
FIG. 31 illustrates a marked patient for detection by the photographic detection system.

In addition to the reference points, the patient can also be marked to define an edge of the forearm support or other features. With reference to FIG. 31, the doctor can mark the patient's arm 703 with a pen 705 or with stickers 704 to help define a position of the marker or define the locations of the edge of the forearm support or identify and locate other important features. The edge marking can be one or more continuous ink lines 707 or stickers 704 that extend around the patient's arm 703. In other embodiments, the edge or other features can be defined by a series of ink marks or stickers 704 that are connected during the crutch design. The ink lines 707, stickers 704 or other markings can also be placed on the patient to create visible reference points to indicate areas of interest or forearm support design points on the patient.

For example, the patient may have injured areas from an operation that has been closed with stitches and should not be in contact with the forearm support. By providing an opening in the forearm support, the patient's stitches will not be pressed against the forearm support structure. In FIG. 31, one or more stickers 704 have been placed on the arm 703 that can be used to detect physical position as described above. The stickers 704 can also be placed around a injured portion of the patient's body so injured portion and position information can be identified by the forearm support design system and that the forearm support can be accurately designed around any injured surface areas. Notes or symbols can also be placed on the patient's arm 703. For example, the doctor can write information indicating the location of the injury as well as information indicating the locations of bones, joints, tendons and ligaments. These anatomical locations are important in the design of the forearm support and hand grip and are therefore marked on the patient's arm 703. Because photogrammetry uses photographs, the digital pictures will record all stickers 704, lines 707 and other ink markings as well as any visible injuries or light patterns projected onto the arm 703.

In addition to being the proper dimensions, the forearm support must also be strong enough for the required use. In an embodiment, the strength of the forearm support is determined by the geometry of the forearm support and the materials used to fabricate the forearm support. Suitable materials include high strength plastics, such as high strength polyamides, or metals, alloys and composites such as carbon fiber in an epoxy binder.

Figure 32:
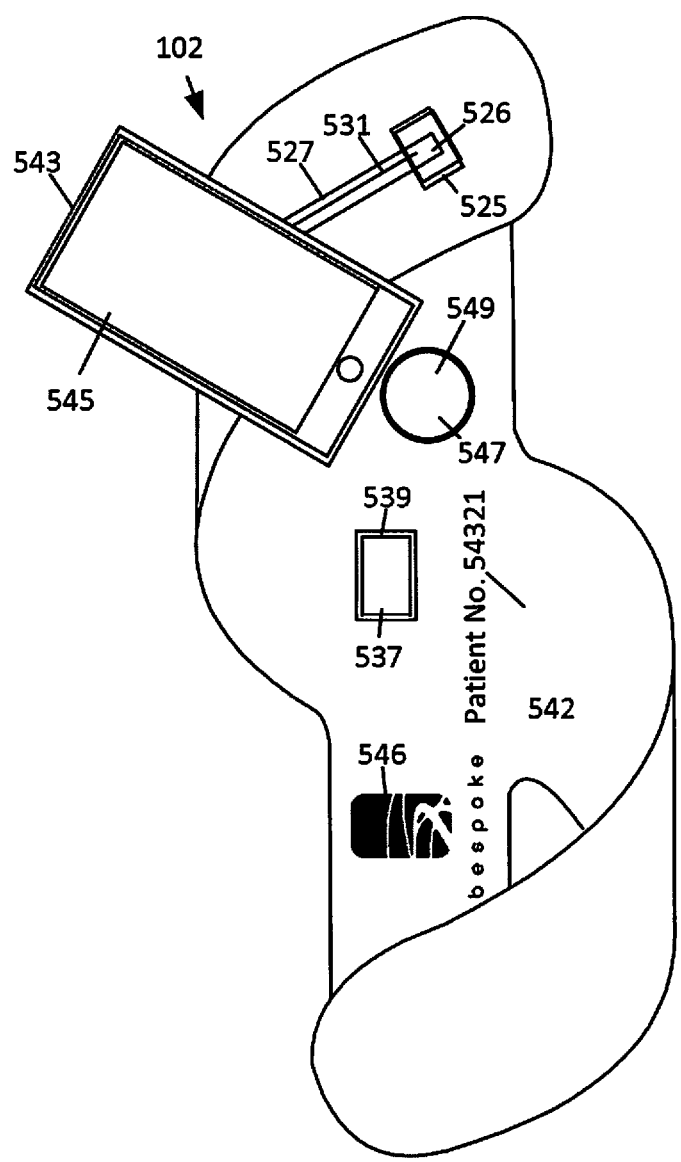
FIG. 32 illustrates an embodiment of the forearm support with additional features.

In addition to designing the forearm support to provide support for the patient's body, additional features can be added to the forearm support design before fabrications. With reference to FIG. 32, the use of additive fabrication allows unique markings and/or patient information to be added to the forearm support design and printed directly into the forearm support during the fabrication process. These markings can include: ornamental images and patterns, patient medical or identification information 542, the logo for the clinic or manufacturer that provided the crutch 546, the date of manufacture, etc.

Other additional features that can be added to the forearm support design include custom mounts on the forearm support at locations that are specified by the designer or physician. The custom mounts may represent positive protrusions, or negative depressions of combinations thereof. The mounts may support functional or cosmetic devices. An example of a forearm support mount 543 would be a mount for a device 545 such as: an iPod, iPad, iPhone, cell phone, remote control device or other portable electronic devices. These devices 545 can be difficult to operate with one hand. By securing any of the devices 545 to the forearm support 102, the patient can operate the device 545 with a free hand, finger or limb. In some embodiments, the positions of these electronic devices 545 can be fixed. In other embodiments, the mounts 543 may be adjustable so that the devices 545 can be optimally positioned by the user.

The mounts on the forearm support and hand grip may also be used for other devices including: sensors, stimulators, actuators and/or electronic devices. An example of a stimulator can be a radio frequency bone stimulator 537 for a fracture delayed union. The mount 539 for the stimulator 537 can be added to the forearm support or hand grip. After the forearm support 102 is fabricated, the stimulator 537 can be easily placed in the mount 539 such that the stimulator 537 can be reproducibly positioned on the forearm support. In an embodiment the bone stimulator 537 may only be placed in the mount 539 for radio frequency therapy or alternatively, if the stimulator 537 is small, it can be left in the mount 539 more permanently. In other embodiments, the forearm support 102 may include similar mounts that can be used for electrical stimulator devices that stimulate muscles electrically to reduce disuse atrophy that occurs with prolonged immobilization of a limb.

In other embodiments, the forearm support 102 can be designed with mounts 547 for sensors 549 that can monitor the physical condition of the patient and/or crutch. For example, the sensors 549 may include a strain sensor that is coupled to a monitoring device that produces a warning when excess force is applied to the forearm support 102. The integrated strain sensor can inform the patient of the excess applied force so that to avoid damage to the crutch or limb. As the patient heals, the excess force level alarm setting can be adjusted by the monitoring device. In an embodiment, the monitoring device can be a personal electronic device such as an iPhone 545 that communicates with the sensor 549 wirelessly through low power RF signals. This feature can be beneficial because it can allow the patient to know the force capabilities of the forearm support 102 and know when excessive force is being applied. The system may adjust the excess force level as the limb heals so that as the patient heals, more force can be applied to the forearm support 102. This feature may allow for less rigid forearm support and hand grip construction since the crutch does not have to be designed for a specific maximum working loading and create a more dynamic bracing concept.

The described devices that are placed in the mounts can be electrical devices which require electrical power and/or a communications pathway. The forearm support 102 may also be designed with an integrated system for securing any necessary cables 531 to the forearm support 102. The cable system can include a recessed area 527 that allows the cable 531 to be held on the forearm support and hand grip. The system may also include a mount 525 for a signal connector 526 to secure the connector 526 to the forearm support 102. This system can prevent the forearm support 102 from having loose cables or wires that can get caught or interfere with the movement of the crutch. Because the medical device mounts can be precisely positioned on the forearm support 102 during the design process, the mounts are integrally formed with the forearm support 102 during the fabrication process.

All of the described markings and mounts can be added to the design of the forearm support 102 and incorporated into the design during the fabrication process without additional processing. No additional work or modification is needed to add the mounts on the crutch. Thus, even with these added mountings and markings, the production time and fabrication cost for the forearm support and hand grip is not increased. The markings and printing can be formed in a surface of the forearm support and hand grip in relief on interior or exterior surfaces of the crutch. No previous bracing technology has allowed for the precision or easy application of the stimulator technology within low profile bracing 100 and accurate placement of sensors, devices and position information.

The forearm support can be designed to have an inner surface that corresponds to the scan data for the patient. In order to provide a comfortable fit for the patient, the inner surface of the forearm support can be designed to be slightly larger or smaller than the surface data for the patient. Different portions of the forearm support can have different offsets between the surface data and the inner forearm design data. Different portions of the forearm support can have different offsets so that some portions of the forearm support are designed with an inner surface that more closely matches the surface data for the patient and other portions of the forearm support that have an inner surface that are further offset away from or inward from the surface data for the patient. In an embodiment, a positive offset indicates a portion of the forearm support that is expanded away from the surface data so that there is more room between the inner surface of the forearm support and the skin of the patient. A negative offset indicates that a portion of the forearm support is smaller than the surface data so these regions of the forearm support are compressed against the patient. In an embodiment, the offset can be a linear taper of about 1 mm-6 mm offset on side of the palm extending as far as the forearm support extends on the back of the hand. The offsets can be described in terms of their maximum offset, over what area the offset is at a maximum value, and the distance where the values return to nominal, which can be called the falloff.

In addition to offsets, in other embodiments, the edges of the forearm support can be flared away from the patient so that one or more portions of the forearm support are not directly adjacent to the patient's skin that can be uncomfortable. In an embodiment, the edge flaring for one or more portions of the forearm support can have a max value=3.5 mm and a min value=1 mm. A portion of the distal edge adjacent the hand portion of the forearm support can be flared to allow comfortable hand movement.

Figure 33:
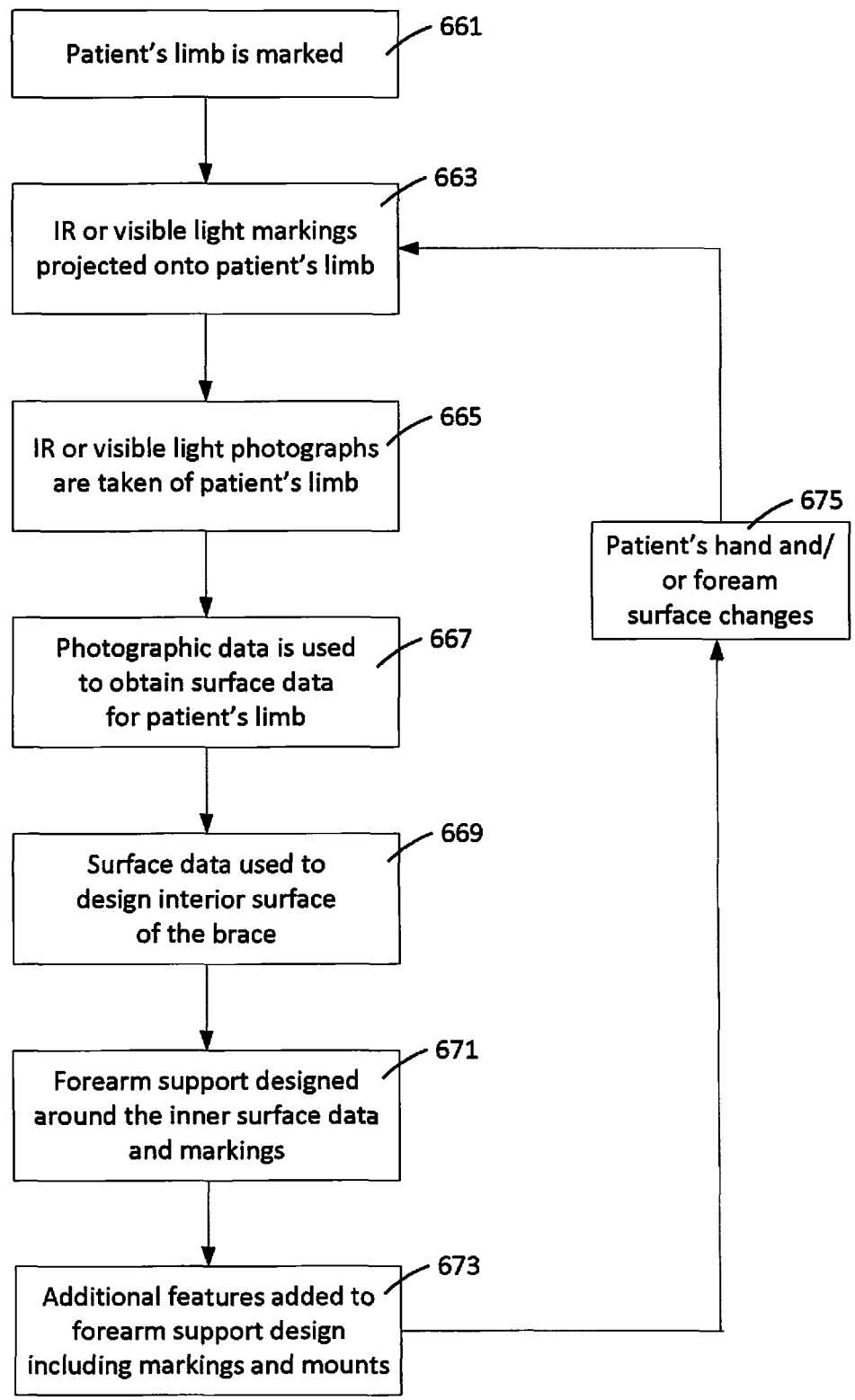
FIG. 33 illustrates a flow chart for fabricating a forearm support.

With reference to FIG. 33, a flowchart of the process steps for fabricating a forearm support and hand grip for a crutch is illustrated. As discussed above, the patient's limb can be marked 661 with any type of marking device such as a sticker or ink that can be photographed. The markings can indicate a surface location, the location of the injury, edges, sensitive areas, locations of stitches, and other body features. The patient's limb can be illuminated with IR or visible light in a pattern such as dots, lines, grids or any other plurality of light points 663. The limb can be photographed with IR and/or visible light cameras 665. From the photographic data, the surface data for the patient's forearm and hand can be obtained 667. In other embodiments the limb may not be illuminated with an IR or visible light pattern and the surface data can be obtained by the natural markings on the patient's skin. The surface data can be used to create a digital representation of the limb of the patient.

The surface data or digital representation of the limb of the patient can be used to design interior surfaces of a forearm support 669. With the limb surface data and additional information about the limb injury, the forearm support can be designed to prevent specific types of movements and avoid contact with specific areas of the limb 670. In order to provide a comfortable fit, the interior surfaces of the forearm support can be designed to be slightly larger than the surface data of the limb of the patient and all exposed edges of the forearm support can have large radii to remove any sharp surfaces. Thus, the interior surface may correspond to the digital representation of the limb of the patient rather than being an exact surface match. If the limb changes in size but remains injured, a new crutch may need to be fabricated to provide the required support and restricted movement. The described process can be repeated to fabricate a new crutch based upon new photographs of the patient's limb.

After the forearm support and hand grip are designed, the crutch design data is transmitted to a three dimensional fabrication machine that constructs the forearm support. In an embodiment, the three dimensional fabrication machine is rapid prototyping, rapid manufacturing, layered manufacturing, 3D printing, laser sintering, and electron beam melting (EBM), fused material deposition (FDM), CNC, etc. The fabrication machine produces a three dimensional single or multiple piece structure that can be plastic, metal or a mix of different materials by forming planar cross section layers of the structure on previously formed planar cross section layers. This layered fabrication process is continued from one end of the structure to the opposite end until the structure is completely fabricated.

When the forearm support and hand grip are fabricated using a three dimensional printing machine, these components are formed by depositing a plurality of parallel planar layers of material with each layer fused to the adjacent layer. Each layer of material used to form the forearm support and hand grip can have a predetermined and uniform thickness. In order to optimize the efficiency of the forearm support and hand grip fabrication, it can be desirable to minimize the number of parallel planar layers used to create the forearm support and hand grip. This minimizes the number of layers that are formed to create the forearm support and hand grip and optimizes the fabrication efficiency. In an embodiment, the forearm support and hand grip design information can be placed in a virtual box having square corners. The parallel planar layers formed to create the forearm support and hand grip can be perpendicular to the shortest dimension of the forearm support and hand grip that can be the thickness of the box.

After the forearm support has been formed, additional processing can be performed on the inner surface to increase the smoothness. The inner surface can be tumbled, sanded, polished, or other processes can be used to create the smooth inner surfaces of the forearm support. These processes can be performed by hand or by a machine. In other embodiments, a filler material can be deposited on the inner surface of the forearm support to create a smooth surface. For example, the inner surface may be painted and the paint may fill the uneven surfaces and dry to a smooth surface. Alternatively, the inner surface can be heated to cause the forearm support material to reflow and create a smooth inner surface.

The use of a photographic process has many advantages over other surface scanning technologies such as laser scanning. The process for transposing the locations of features from the patient to the forearm support, hand grip or device is simplified because the doctor can apply location marks to the patient directly or on a form fitting covering. Thus, the locations of the features are much more likely to be accurately placed on the final product. The equipment costs are also reduced because the digital cameras, computers and electronic memory are inexpensive. The photographic equipment is also portable, so it can be easily transported to patient's location. The digital data can then be transmitted electronically to a fabrication machine located at a guild. Alternatively, the digital device data can be recorded onto a disk and transmitted to the fabrication machine.

The present disclosure, in various embodiments, includes components, methods, processes, systems and/or apparatus substantially as depicted and described herein, including various embodiments, subcombinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation. Rather, as the following claims reflect, inventive aspects lie in less than all features of any single foregoing disclosed embodiment.

What is claimed is:

1. A custom crutch designed to be virtually fitted on a forearm of a patient prior to fabrication comprising:

an elongated member having a distal portion and a proximal portion;

a hand grip coupled to the proximal portion of the elongated member; and a forearm support coupled to the proximal portion of the elongated member;

wherein the forearm support includes an elongated body and a first curved member and a second curved member that are rigidly coupled to the elongated body, wherein the first curved member is attached to a proximal portion of the elongated body and the second curved member is attached to a separated location near a central portion of the elongated body to define an elongate inner surface of the forearm support, and the inner surface of the forearm support is adapted to correspond a digital representation of the forearm of the patient and wherein the digital representation of the forearm is obtained by photogrammetrically processing a plurality of digital images of the forearm of the patient.

2. The custom crutch of claim 1 wherein the hand grip is rigidly coupled to the elongated body of the forearm support.

3. The custom crutch of claim 2 wherein the first curved member and the second curved member are oriented in a spiral configuration adapted to around the digital representation of the forearm of the patient.

4. The custom crutch of claim 1 wherein the hand grip is rigid and includes an outer surface that is adapted to correspond to a digital representation of the palmar surface of a hand of the patient.

5. The custom crutch of claim 1 wherein the hand grip includes an outer surface that is adapted to correspond to a digital representation of the palmar surface of a hand of the patient.

6. The custom crutch of claim 1 wherein the elongated member is a telescoping structure having a first tubular member and a second tubular member within the first tubular member.

7. The custom crutch of claim 1 further comprising: a hinge coupled to the elongated body of the forearm support wherein the hinge allows the elongated member to rotate relative to the forearm support.

8. The custom crutch of claim 7 wherein the hinge includes a locking mechanism that includes a first setting that rigidly holds the hinge at a first angle and a second setting that holds the hinge at a second angle.

9. The custom crutch of claim 1 wherein the hand grip and the forearm support are integrated into a single structure.

10. The custom crutch of claim 1 wherein the elongated body of the forearm support at least partially surrounds the proximal portion of the elongated member.

11. A custom crutch designed to be virtually fitted on a forearm of a patient prior to fabrication comprising:

an elongated member having a distal portion and a proximal portion;

a hand grip coupled to the proximal portion of the elongated member; and a forearm support body rigidly coupled to a first curved member and a second curved member, the first curved member turning upward and inward and the second curved member turning downward and outward to define a spiral configuration, wherein an inner surface of the forearm support is adapted to correspond to a digital representation of the forearm of the patient and wherein the digital representation of the forearm is obtained by photogrammetrically processing a plurality of digital images of the forearm of the patient.

12. The custom crutch of claim 11 wherein the hand grip has a palmar surface that is adapted to correspond to a digital representation of a palm of the patient.

13. The custom crutch of claim 11 wherein thicknesses of the first curved member and the second curved member are greater than 0.05 inch and less than 0.50 inch.

14. The custom crutch of claim 11 wherein a pitch of the first curved member and the second curved member in the spiral configuration is greater than 2 inches and less than 6 inches.

15. The custom crutch of claim 11 wherein the forearm support is fabricated from a plurality of fused planar layers that are parallel to each other.

16. The custom crutch of claim 15 wherein the spiral shape of the forearm support defines a center axis and the plurality of fused planar layers are approximately parallel to the center axis.

17. The custom crutch of claim 11 wherein the elongated member is a telescoping structure having a first tubular member and a second tubular member within the first tubular member.

18. The custom crutch of claim 11 further comprising: a hinge coupled to the elongated body of the forearm support wherein the hinge allows the elongated member to rotate relative to the forearm support.

19. The custom crutch of claim 18 wherein the hinge includes a locking mechanism that includes a first setting that rigidly holds the hinge at a first angle and a second setting that holds the hinge at a second angle.

20. The custom crutch of claim 11 wherein the hand grip and the forearm support are integrated into a single structure.

* * * * *